US011285483B2

(12) United States Patent
Kikuchi et al.

(10) Patent No.: US 11,285,483 B2
(45) Date of Patent: Mar. 29, 2022

(54) CELL OBSERVATION SYSTEM AND CELL OBSERVATION METHOD

(71) Applicants: HAMAMATSU PHOTONICS K.K., Hamamatsu (JP); NATIONAL UNIVERSITY CORPORATION HAMAMATSU UNIVERSITY SCHOOL OF MEDICINE, Hamamatsu (JP)

(72) Inventors: Hirotoshi Kikuchi, Hamamatsu (JP); Shigetoshi Okazaki, Hamamatsu (JP); Hidenao Yamada, Hamamatsu (JP); Yusuke Ozaki, Hamamatsu (JP); Amane Hirotsu, Hamamatsu (JP); Daisuke Yamashita, Hamamatsu (JP)

(73) Assignees: HAMAMATSU PHOTONICS K.K., Hamamatsu (JP); NATIONAL UNIVERSITY CORPORATION HAMAMATSU UNIVERSITY SCHOOL OF MEDICINE, Hamamatsu (JP)

(*) Notice: Subject to any disclaimer, the term of this patent is extended or adjusted under 35 U.S.C. 154(b) by 356 days.

(21) Appl. No.: 16/122,048

(22) Filed: Sep. 5, 2018

(65) Prior Publication Data
US 2019/0070608 A1 Mar. 7, 2019

(30) Foreign Application Priority Data
Sep. 6, 2017 (JP) .............................. JP2017-171039

(51) Int. Cl.
*G01N 15/14* (2006.01)
*C12Q 1/04* (2006.01)
(Continued)

(52) U.S. Cl.
CPC .......... *B01L 3/502761* (2013.01); *C12Q 1/04* (2013.01); *G01N 15/147* (2013.01);
(Continued)

(58) Field of Classification Search
None
See application file for complete search history.

(56) References Cited

U.S. PATENT DOCUMENTS 5,521,699 A 5/1996 Kosaka et al.
2002/0058332 A1* 5/2002 Quake ............... B01L 3/502715
435/288.5
(Continued)

FOREIGN PATENT DOCUMENTS

EP 0466168 A2 1/1992
EP 0539022 A2 4/1993
(Continued)

OTHER PUBLICATIONS

Daniel Malacara et al., "Interferogram Analysis for Optical Testing," Taylor & Francis Group, 2005, Second Edition, Chapter 6.
(Continued)

*Primary Examiner* — Neil N Turk
(74) *Attorney, Agent, or Firm* — Faegre Drinker Biddle & Reath LLP

(57) ABSTRACT

A cell observation system observes a cell moving in a flow path with a fluid, and includes a first observation apparatus, a second observation apparatus, and a control device. The first observation apparatus includes an objective lens and a line camera. The second observation apparatus includes an objective lens and an area camera. The control device analyzes first imaging data output from the first observation apparatus to determine whether the cell satisfies a specific condition, instructs the area camera to output second imaging data of the cell determined to satisfy the specific con-
(Continued)

dition, and analyzes the second imaging data output from the second observation apparatus to determine whether the cell is a specific cell.

3 Claims, 18 Drawing Sheets

(51) Int. Cl.
*B01L 3/00* (2006.01)
*G06K 9/00* (2006.01)
*C12M 1/36* (2006.01)
*G01N 15/10* (2006.01)

(52) U.S. Cl.
CPC ..... *G01N 15/1427* (2013.01); *G01N 15/1434* (2013.01); *G01N 15/1463* (2013.01); *G01N 15/1475* (2013.01); *G06K 9/00127* (2013.01); *B01L 2300/0864* (2013.01); *C12M 41/48* (2013.01); *G01N 2015/1006* (2013.01); *G01N 2015/144* (2013.01); *G01N 2015/149* (2013.01); *G01N 2015/1443* (2013.01); *G01N 2015/1477* (2013.01); *G01N 2015/1488* (2013.01)

(56) References Cited

U.S. PATENT DOCUMENTS

| | | | |
|---|---|---|---|
| 2006/0204071 A1* | 9/2006 | Ortyn | G01N 21/6458 382/133 |
| 2013/0177973 A1 | 7/2013 | Kondo | |

FOREIGN PATENT DOCUMENTS

| | | |
|---|---|---|
| JP | H4-072544 A | 3/1992 |
| JP | H5-079970 A | 3/1993 |
| JP | H7-043307 A | 2/1995 |
| JP | 2008-288806 A | 11/2008 |
| WO | WO-2013/065796 A1 | 5/2013 |
| WO | WO-2016/017533 A1 | 2/2016 |

OTHER PUBLICATIONS

P. Hariharan et al., "Digital phase-shifting interferometry: a simple error-compensating phase calculation algorithm," Applied Optics, Jul. 1987, pp. 2504-2506, vol. 26, No. 13.

Kenichi Hibino et al., "Phase-shifting algorithms for nonlinear and spatially nonuniform phase shifts," Journal of Optical Society of America, Apr. 1997, pp. 918-930, vol. 14, No. 4.

* cited by examiner

CELL OBSERVATION SYSTEM AND CELL OBSERVATION METHOD

BACKGROUND OF THE INVENTION

Field of the Invention

The present disclosure relates to a cell observation system and a cell observation method.

Related Background Art

Patent Document 1 discloses an invention in which an area camera receives Doppler-shifted light by a cell moving in a flow path with a fluid to capture an image of the cell, and a three-dimensional image of the cell is generated by processing the imaging data. For example, the number of nucleoli existing in a cell nucleus can be used as an index of determining whether the cell is a cancer cell, however, there is a need to acquire a three-dimensional image in order to count the plurality of nucleoli which are three-dimensionally arranged. Therefore, in the invention disclosed in Patent Document 1 that can acquire the three-dimensional image of the cell, circulating tumor cells (CTC) in the blood can be identified with high accuracy with respect to normal cells of red blood cells and white blood cells compared to a case where simply the two-dimensional image is acquired.

The CTC is a cell which is separated from a primary tumor tissue or a metastatic tumor tissue and enters the blood, and a very small amount of CTC is found in peripheral blood of a solid cancer patient at a rate of one out of 1,000,000. In the cell called a CTC, a cell having a metastatic ability to other organs is considered to be included.

In the invention disclosed in Patent Document 1, it is necessary to employ an area camera having a high-speed imaging function. The commercially available area cameras are roughly classified into a type of accumulating imaging data in a built-in memory (hereinbelow, referred to as "image accumulating type") and a type of sequentially transferring imaging data to the outside of the area camera main body (hereinafter; referred to as "image transferring type"). The area camera of the image accumulating type has a built-in memory which can transfer data at a high speed, and temporally accumulates the imaging data in the memory. Then, the area camera of the image accumulating type can selectively output the necessary imaging data among the accumulated imaging data toward an external storage device (for example, a storage device of a computer). In contrast, the area camera of the image transferring type sequentially outputs the imaging data toward the external storage device.

In general, the area camera of the image accumulating type is suitable to a high speed imaging compared to the area camera of the image transferring type. The reason is that, for example, a speed of data accumulation into the built-in memory in the area camera of the image accumulating type is 25 GB/s while a speed of data transfer from the area camera of the image transferring type to the external storage device is 0.5 GB/s.

From this viewpoint, in the invention disclosed in Patent Document 1, it is preferable to use the area camera of the image accumulating type which can capture an image at a high speed.

Patent Document 1: International Publication No. 2013/065796
Patent Document 2: International Publication No. 2016/017533

Non Patent Document 1: Daniel Malacara et al., "Interferogram Analysis for Optical Testing", Taylor & Francis Group, Second Edition, Chapter 6 (2005)
Non Patent Document 2: P. Hariharan et al., "Digital phase-shifting interferometry: a simple error-compensating phase calculation algorithm", Appl. Opt. Vol. 26, pp. 2504-2506 (1987)
Non Patent Document 3: Kenichi Hibino et al., "Phase-shifting algorithms for nonlinear and spatially nonuniform phase shifts", J. Opt. Soc. Am. A Vol. 14, pp. 918-930 (1997)

SUMMARY OF THE INVENTION

However, the area camera of the image accumulating type has a problem in that the imaging time is restricted by a capacity of the built-in memory. For example, Phantom v2512, which is an area camera of Vision Technology Co., can capture images of data amount of 25 GB per one second and accumulate the images in the built-in memory. This corresponds to a performance in which an image of 1280× 800 pixels per one frame can be captured at a speed of 25,000 frames per second. Therefore, in a case where the capacity of the memory provided in the area camera is 72 GB, imaging data of about 3 seconds (=72 GB/(25 GB/s)) can be accumulated. An imaging available time is tr. Thereafter, for example, the imaging data accumulated in the built-in memory of the area camera is transferred to the computer with about 150 seconds. The imaging is not possible during a period of 150 seconds. The period during which the imaging is not possible becomes a dead time (td).

In the invention disclosed in Patent Document 1, in a case where a moving speed of the cell in the flow path is assumed as 2 mm/sec, and the imaging is performed at a speed of 25,000 frames/sec using the area camera of the image accumulating type which can capture an image at a high speed as described above, only 100 cells per second can be observed at most. Therefore, only 300 cells can be observed at most in 3 seconds during which the imaging can be continuously performed. That is, considering a dead time period of about 150 seconds when the imaging is not possible, only 300 cells can be observed at most for 153 seconds. In the invention disclosed in Patent Document 1, the speed of cell observation is restricted by the performance of the area camera, and it is difficult to observe a large number of cells.

An object of an embodiment is to provide a cell observation system and a cell observation method which can observe a large number of cells and can be suitably used to identify a specific cell (cancer cell).

An embodiment relates to a cell observation system. The cell observation system is a system for observing a cell moving in a flow path with a fluid, and includes (1) a first observation apparatus including a line camera and a first optical system, and for capturing an image of the cell using the line camera to acquire and output first imaging data, (2) a second observation apparatus including an area camera and a second optical system, and for capturing an image of the cell using the area camera to acquire second imaging data, and (3) a control device for analyzing the first imaging data output from the first observation apparatus to determine whether the cell satisfies a specific condition, instructing the area camera to output the second imaging data of the cell determined to satisfy the specific condition, and analyzing the second imaging data output from the second observation apparatus to determine whether the cell is a specific cell.

An embodiment relates to a cell observation method. The cell observation method is a method for observing a cell moving in a flow path with a fluid, and includes (1) a first determination step of determining whether the cell satisfies a specific condition by analyzing first imaging data output from a first observation apparatus, the first observation apparatus including a line camera and a first optical system, and for capturing an image of the cell using the line camera to acquire and output the first imaging data, (2) an instruction step of instructing a second observation apparatus to output second imaging data for the cell determined to satisfy the specific condition, the second observation apparatus including an area camera and a second optical system, and for capturing an image of the cell using the area camera to acquire the second imaging data, and (3) a second determination step of analyzing the second imaging data output from the second observation apparatus to determine whether the cell is a specific cell.

According to the embodiment, it is possible to observe a large number of cells, and identify a specific cell with efficiency.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DETAILED DESCRIPTION

Hereinafter, embodiments of a cell observation system and a cell observation method will be described in detail with reference to the accompanying drawings. In the description of the drawings, the same elements will be denoted by the same reference signs, without redundant description. Further, the present invention is not limited to these examples.

First Embodiment

Figure 1:
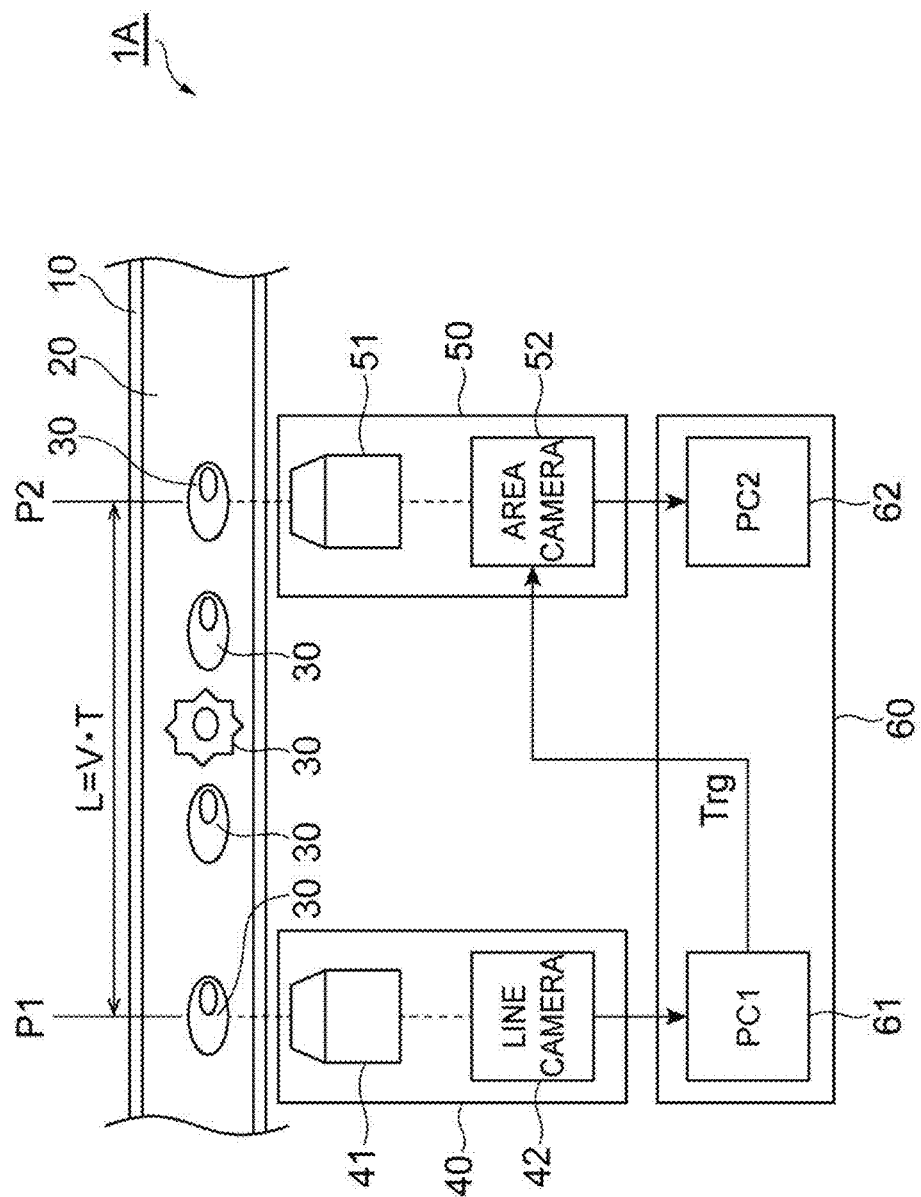
FIG. 1 is a diagram illustrating a configuration of a cell observation system 1A of a first embodiment.

FIG. 1 is a diagram illustrating a configuration of a cell observation system 1A of a first embodiment. The cell observation system 1A is used to observe a cell 30 which moves in a flow path 10 with a fluid 20. The cell observation system 1A includes a first observation apparatus 40, a second observation apparatus 50, and a control device 60.

For example, the flow path 10 is a flow cell, the fluid 20 is a culture solution, and the cell 30 is a red blood cell, a white blood cell, a CTC, and the like. The cell 30 is prepared in a state of being suspended in the culture solution. A concentration of the suspension is, for example, $10^6$ pieces/mL. The cell suspension is introduced to the flow path 10. With a sheath flow technique, the cells 30 are aligned in a line and move in the flow path 10. With such a configuration, it is possible to obtain a focused image.

The first observation apparatus 40 includes an objective lens 41 (first optical system) and a line camera 42. The objective lens 41 forms an image of the cell 30 on a light receiving plane of the line camera 42. The line camera 42 is optically coupled to the objective lens 41, and includes the light receiving plane on which a plurality of pixels are arranged one-dimensionally. The arrangement direction of the plurality of pixels on the light receiving plane of the line camera 42 is intersected with a moving direction of the image of the cell on the light receiving plane. The line camera 42 captures the image of the cell 30 to acquire first imaging data, and outputs the data sequentially.

The first imaging data at each time point which is output from the line camera 42 represents a one-dimensional image, and further, since the cell 30 moves, it is possible to represent the images as a two-dimensional image by aligning the first imaging data at the respective time points in order of time. An imaging speed (line/s) of the line camera 42 is set to $f_1$, and the diameter of the cell is set to D, and the number of scanning per one cell is set to N. These parameters satisfy a relation of $f_1 = N(V/D)$.

The second observation apparatus 50 includes an objective lens 51 (second optical system) and an area camera 52. The objective lens 51 forms an image of the cell 30 on a light receiving plane of the area camera 52. The area camera 52 is optically coupled to the objective lens 51, and includes the light receiving plane on which a plurality of pixels are arranged two-dimensionally. The area camera 52 is an image accumulating type which can allow a high speed imaging, and has a built-in memory which can transfer data at a high speed. The area camera 52 captures the image of the cell 30 to acquire second imaging data, and can accumulate the second imaging data in the memory.

The control device 60 includes a computer 61 and a computer 62. The computer 61 is electrically coupled to the line camera 42 and the area camera 52. The computer 62 is electrically coupled to the area camera 52. Each of the computer 61 and the computer 62 may be a general-purpose computer configured to include a CPU (Central Processing Unit) which is a processor, a RAM (Random Access Memory) or a ROM (Read Only Memory) which is a storage medium, an input unit such as a keyboard, a mouse, or the like, and an input-output module. Further, each of the computer 61 and the computer 62 may be configured as a dedicated device using, for example, a microcomputer, an FPGA (Field Programmable Gate Array), or the like.

The computer 61 inputs the first imaging data output from the line camera 42 of the first observation apparatus 40 and analyzes the first imaging data so as to detect a position of the cell and to determine whether the cell satisfies a specific condition (first determination step). The computer 61 outputs a trigger signal Trg to instruct the area camera 52 of the second observation apparatus 50 to output the second imaging data of the cell 30 determined to satisfy the specific condition (instruction step). The trigger signal Trg is input to the area camera 52. Then, the computer 62 inputs the second imaging data output from the area camera 52 of the second observation apparatus 50 which receives an output instruction by the trigger signal Trg, and analyzes the second imaging data so as to determine whether the cell 30 is a specific cell (cancer cell) (second determination step).

Here, a frequency ft (pieces/s) of appearance of the cell which is determined to satisfy the specific condition in the first determination step is preferably 1/td or less.

The determination in the first determination step of whether the cell satisfies the specific condition is performed for the similar purpose to the determination in the second determination step of whether the cell is the specific cell. However, while the determination in the first determination step is based on the analysis of the first imaging data of the line camera 42, the determination in the second determination step is based on the analysis of the second imaging data of the area camera 52, and thus is performed at a high accuracy. That is, in the determination in the second determination step, a cell determined as suspicious as the specific cell (cancer cell) in the first determination step is subjected to an accurate determination on whether it is the specific cell.

A specific configuration of the first observation apparatus 40 and a content of an analysis process of the first imaging data will be described below in detail. The configuration disclosed in Patent Document 1 may be employed as a specific configuration of the second observation apparatus 50 and a content of an analysis process of the second imaging data. The configuration disclosed in Patent Document 2 may be employed as the content of the determination process in each of the first determination step and the second determination step.

In the embodiment, the area camera 52 captures an image at a position P2 on the downstream side from an imaging position P1 of the line camera 42, with respect to the moving direction (the right direction in the drawing) of the cell 30 in the flow path 10. The area camera 52 receives the output instruction (the trigger signal Trg) from the computer 61 of the control device 60 to start the imaging, and accumulates the second imaging data obtained by capturing the image of the cell over a predetermined period of time in the built-in memory. Then, after ending the imaging over the predetermined period of time, the area camera 52 outputs the second imaging data accumulated in the built-in memory to the computer 62. The area camera 52 erases the second imaging data accumulated in the built-in memory after sending the second imaging data to the computer 62.

Figure 2:
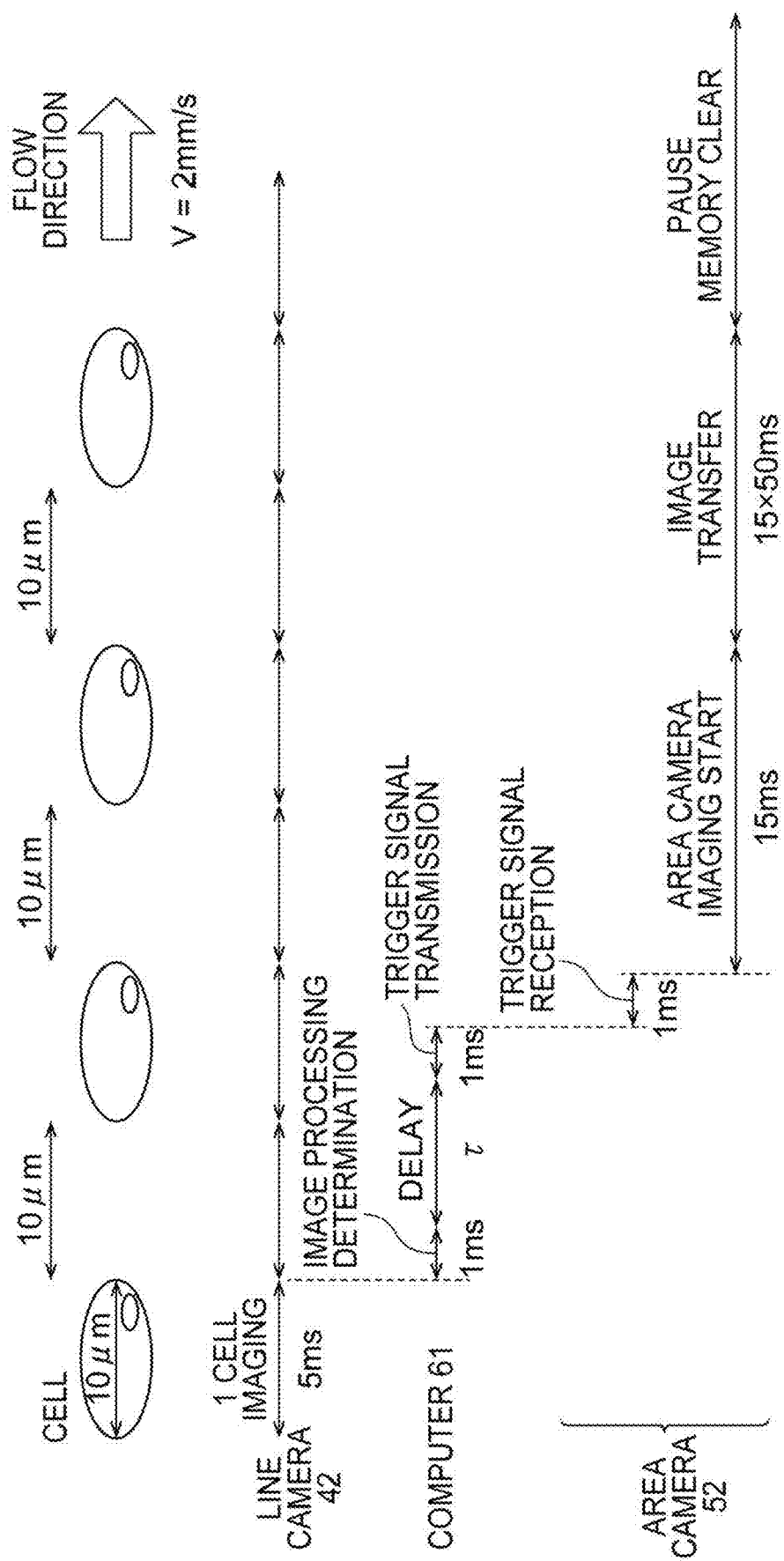
FIG. 2 is a timing chart illustrating an operation example of the cell observation system 1A of the first embodiment.

FIG. 2 is a timing chart illustrating an operation example of the cell observation system 1A of the first embodiment. In the operation example, a moving speed V of the cell in the flow path is set to 2 mm/s, and the size of the cell is set to 10 μm.

In order to generate a two-dimensional image of the cell on the basis of the first imaging data output from the line camera 42, there is needed the first imaging data for at least 5 ms. A time required for the process of the first determination step in the computer 61 is set to 1 ms, and the instruction step is set to be performed after a delay time τ. In the instruction step, a time required for the transmission process of the trigger signal Trg in the computer 61 is set to 1 ms, and a time required for the reception process of the trigger signal Trg in the area camera 52 is set to 1 ms. Thereafter, the area camera 52 receiving the trigger signal starts the imaging. A time required for the imaging in the area camera 52 is set to 15 ms in order to secure a margin before and after the cell. Then, the second imaging data is sent out from the area camera 52 to the computer 62 after the imaging ends. Since a time required for sending out the imaging data takes 50 times the time required for the imaging, the time required for sending out the second imaging data is set to 750 ms (=15 ms×50).

In the operation example, a time T from a start time point of the imaging of a certain cell by the line camera 42 to a start time point of the imaging of the cell by the area camera 52 is 8 ms+τ. The time T, a distance L from the position P1 to the position P2 along the flow path 10, and the moving speed V of the cell satisfy a relation of L=V·T. The delay time τ is set according to the distance L and the moving speed V.

In the embodiment, all the cells 30 flowing in the flow path 10 are imaged by the line camera 42 of the first observation apparatus 40. Then, all the cells 30 flowing in the flow path 10 are determined by the computer 61 on whether the specific condition is satisfied, that is, whether there is a cell suspected as a specific cell, on the basis of the first imaging data which is sequentially output from the line camera 42 (first determination step).

The cell 30 which is determined as suspicious as a specific cell by the computer 61 is selectively imaged by the area camera 52 of the second observation apparatus 50. Then, the computer 62 more strictly determines whether the cell 30 is a specific cell on the basis of the second imaging data output from the area camera 52 (second determination step).

In this way, all the cells are determined on whether there is a cell suspected as a specific cell on the basis of the first imaging data of the line camera 42 which has a less amount of data transfer to the outside and does not take a time for transfer. On the other hand, only a cell suspected as a specific cell is determined on whether the cell is a specific cell on the basis of the second imaging data of the area camera 52 which has a large amount of data transfer to the outside and takes a time for transfer. Therefore, in the embodiment, it is possible to observe a large number of cells and to efficiently identify a specific cell (cancer cell).

Second Embodiment

Figure 3:
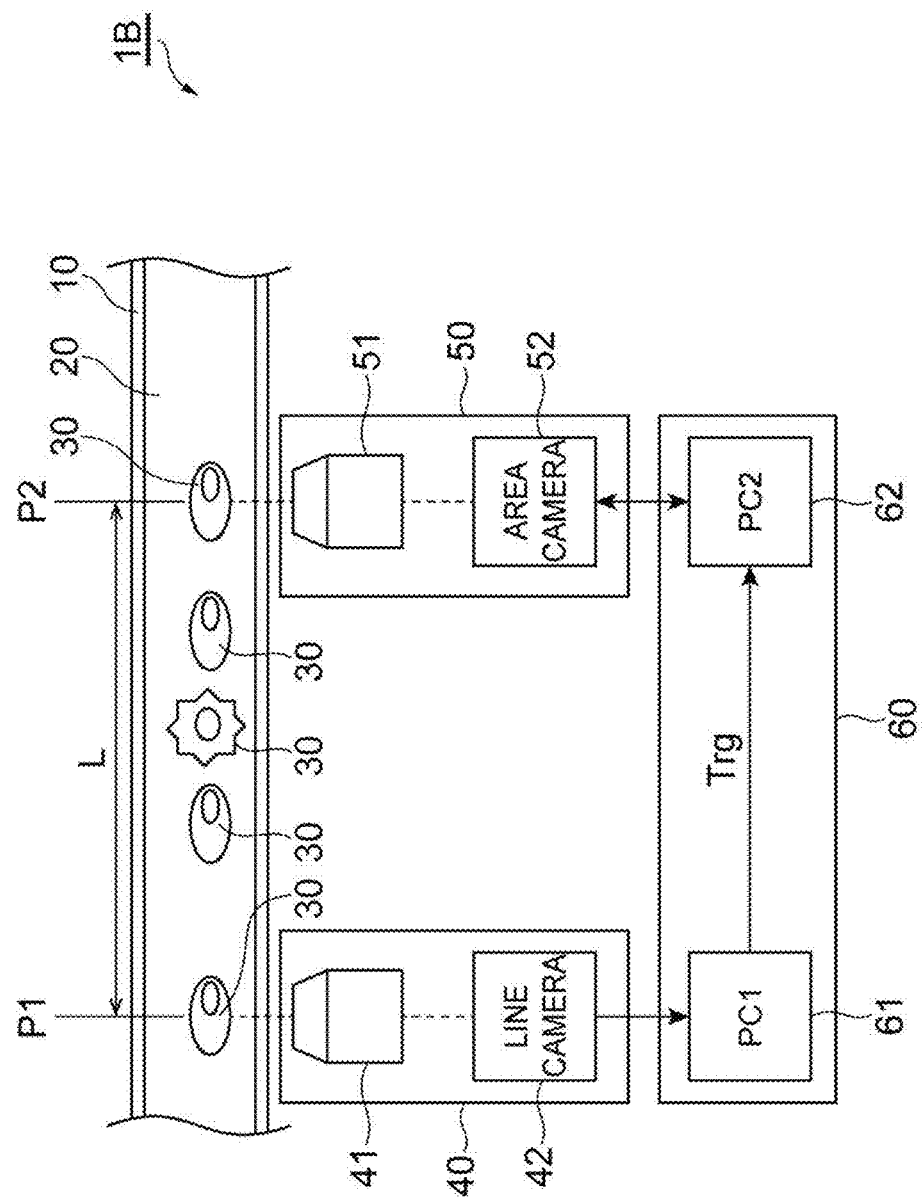
FIG. 3 is a diagram illustrating a configuration of a cell observation system 1B of a second embodiment.

FIG. 3 is a diagram illustrating a configuration of a cell observation system 1B of a second embodiment. The second embodiment is different from the first embodiment in the configuration of the control device 60. The control device 60 in the second embodiment includes the computer 61 and the computer 62. The computer 61 is electrically coupled to the line camera 42. The computer 62 is electrically coupled to the area camera 52. The computer 61 and the computer 62 are electrically coupled to each other.

The computer 61 inputs the first imaging data which is output from the line camera 42 of the first observation apparatus 40, and analyzes the first imaging data so as to detect a position of the cell and to determine whether the cell satisfies a specific condition (first determination step). The computer 61 outputs the trigger signal Trg to instruct the area camera 52 of the second observation apparatus 50 to output the second imaging data of the cell 30 determined to satisfy the specific condition (instruction step).

The trigger signal Trg is input to the computer 62, and input from the computer 62 to the area camera 52. Then, the computer 62 inputs the second imaging data output from the area camera 52 of the second observation apparatus 50 which receives the output instruction by the trigger signal Trg, and analyzes the second imaging data so as to determine whether the cell 30 is a specific cell (second determination step).

In the second embodiment, the passage of the trigger signal Trg is different from the first embodiment, but the similar effect is achieved by the similar operation to the first embodiment.

Third Embodiment

Figure 4:
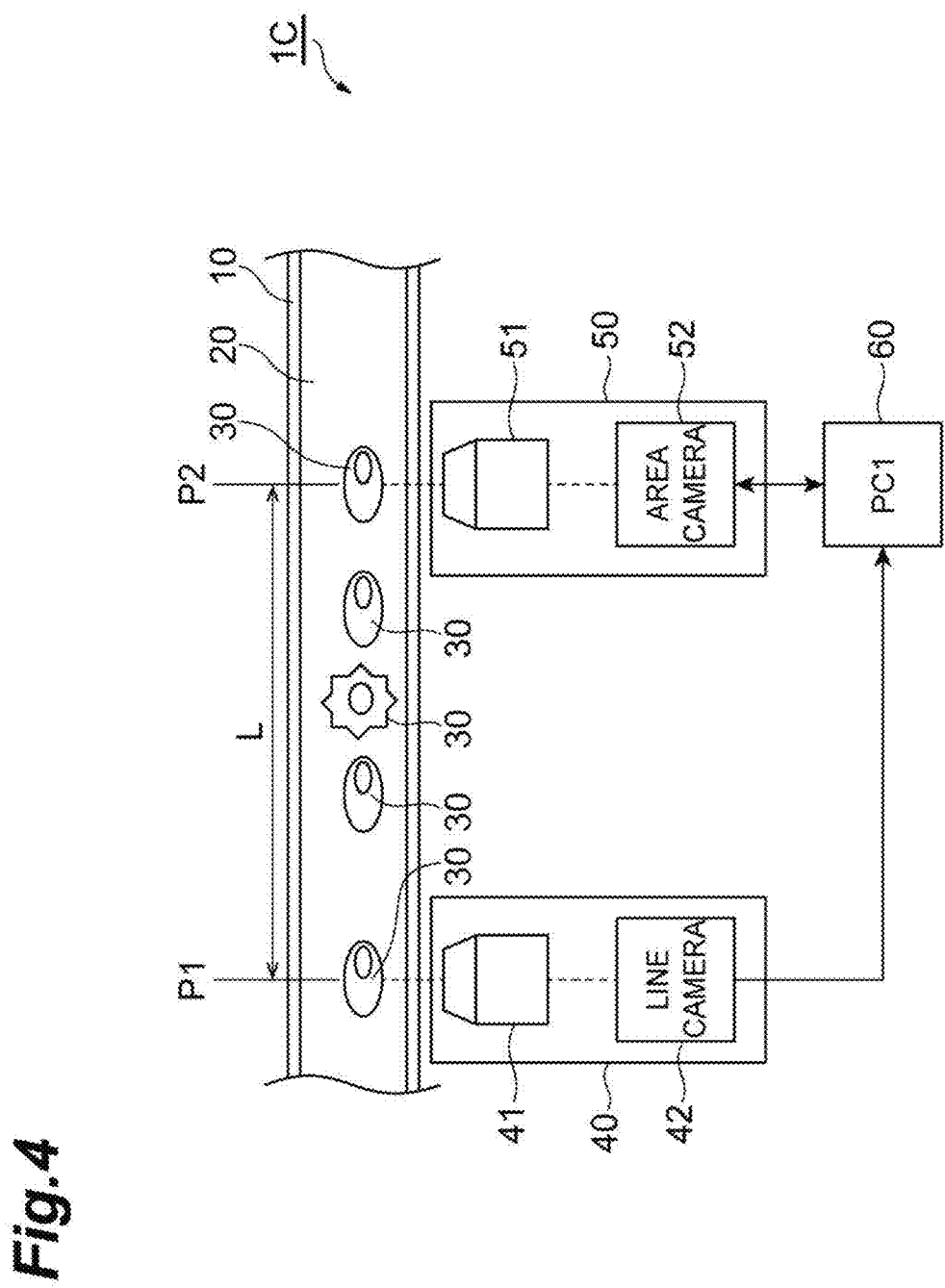
FIG. 4 is a diagram illustrating a configuration of a cell observation system 1C of a third embodiment.

FIG. 4 is a diagram illustrating a configuration of a cell observation system 1C of a third embodiment. The third embodiment is different from the first and second embodiments in the configuration of the control device 60. The control device 60 in the third embodiment includes one computer which is electrically coupled to both the line camera 42 and the area camera 52.

The control device 60 inputs the first imaging data which is output from the line camera 42 of the first observation apparatus 40, and analyzes the first imaging data so as to detect a position of the cell and to determine whether the cell satisfies the specific condition (first determination step). The control device 60 outputs the trigger signal Trg to instruct the area camera 52 of the second observation apparatus 50 to output the second imaging data of the cell 30 determined to satisfy the specific condition (instruction step).

The trigger signal Trg is input to the area camera 52. Then, the control device 60 inputs the second imaging data output from the area camera 52 of the second observation apparatus 50 which receives the output instruction by the trigger signal Trg, and analyzes the second imaging data so as to determine whether the cell 30 is a specific cell (second determination step).

Even in the third embodiment, the similar effect is achieved by the similar operation to the first and second embodiments.

Fourth Embodiment

Figure 5:
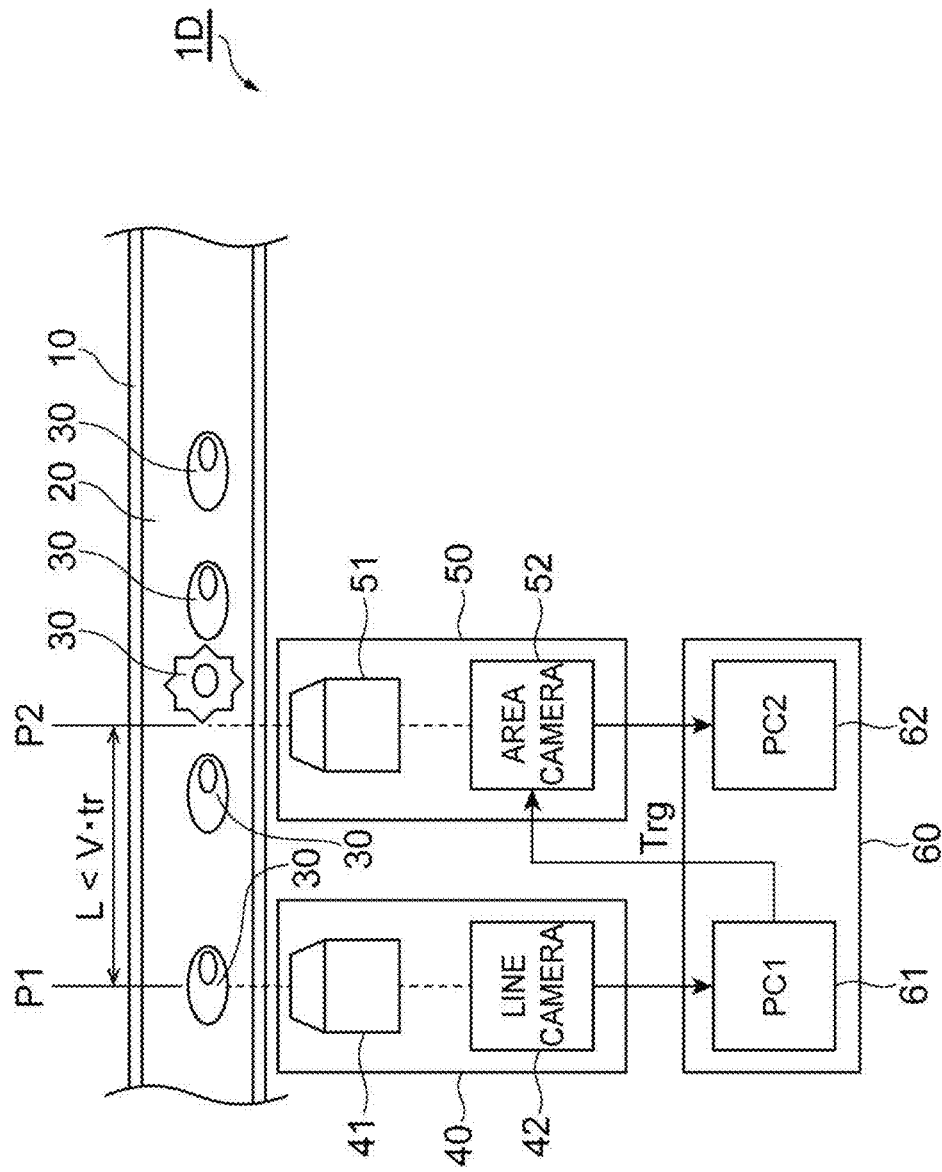
FIG. 5 is a diagram illustrating a configuration of a cell observation system 1D of a fourth embodiment.

FIG. 5 is a diagram illustrating a configuration of a cell observation system 1D of a fourth embodiment. The fourth embodiment is different from the first embodiment in the configuration and the operation of the area camera 52, and in the distance L from the position P1 to the position P2 along the flow path 10.

The area camera 52 in the first embodiment starts the imaging when receiving the trigger signal Trg, accumulates the second imaging data obtained by the imaging of the cell over a predetermined period of time in the built-in memory, and outputs the second imaging data to the computer 62 after the imaging performed over the predetermined period of time ends. In contrast, the area camera 52 in the fourth embodiment sequentially stores the second imaging data at each time point in a built-in memory of a ring buffer type, and outputs the second imaging data over a predetermined period of time which is stored in the built-in memory when receiving the trigger signal Trg.

The memory of the ring buffer type accumulates data sequentially from a certain address, and when the last address is reached, the memory returns to the start address and keeps on accumulating data sequentially. At an address where the data is already accumulated, the memory of the ring buffer type overwrites new data with the already accumulated data. Therefore, the built-in memory of the ring buffer type can accumulate the second imaging data of each time point over a time (imaging available time tr) in accordance with a capacity.

In the fourth embodiment, the area camera 52 suspends the accumulating of new second imaging data to the built-in memory when receiving the trigger signal Trg from the computer 61, and outputs the second imaging data over a predetermined period of time in the past among the second imaging data stored in the built-in memory at that time toward the computer 62.

Figure 6:
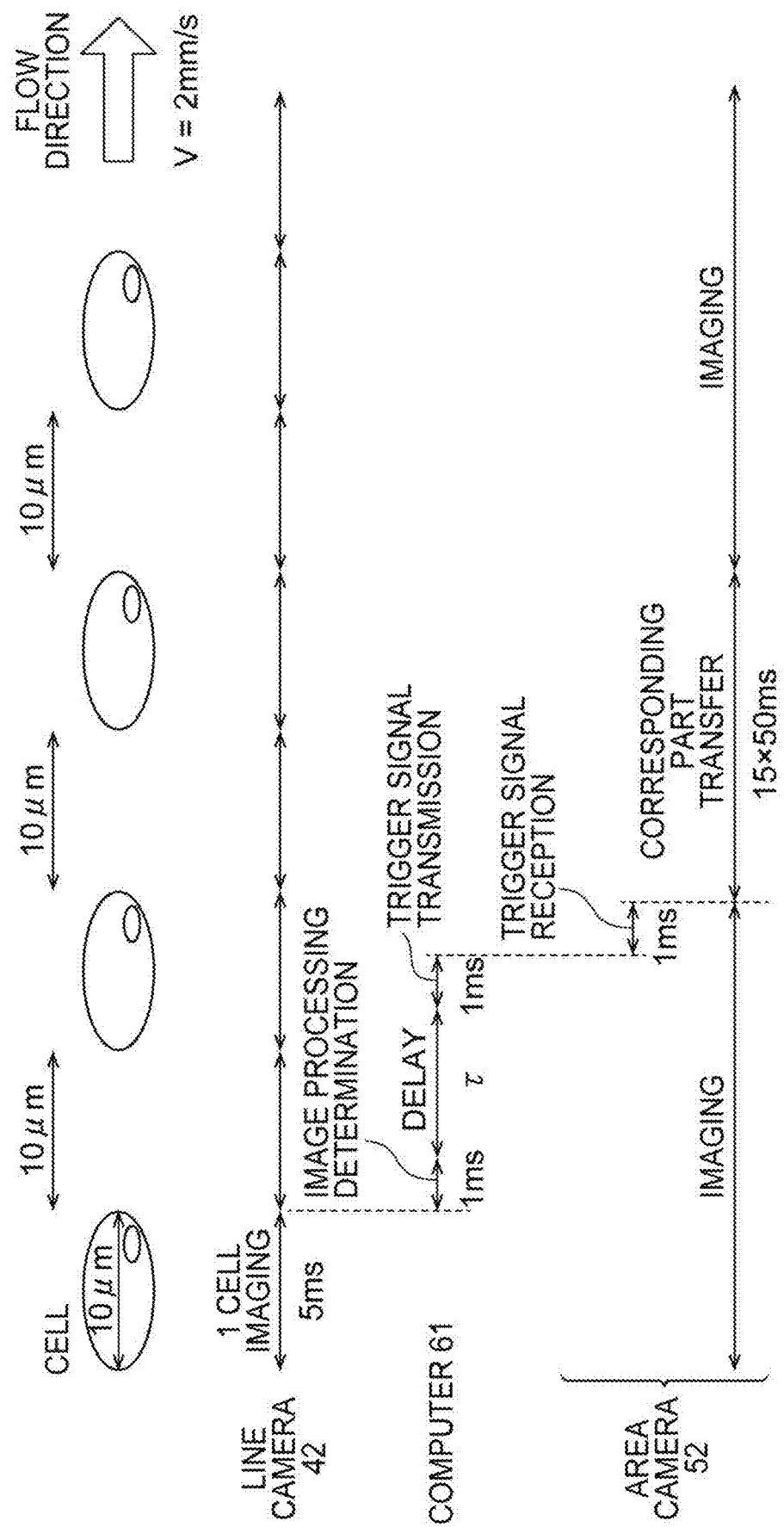
FIG. 6 is a timing chart illustrating an operation example of the cell observation system 1D of the fourth embodiment.

FIG. 6 is a timing chart illustrating an operation example of the cell observation system 1D of the fourth embodiment. Even in the operation example, the moving speed V of the cell in the flow path is set to 2 mm/s, and the size of the cell is set to 10 μm.

In order to generate a two-dimensional image of the cell on the basis of the first imaging data output from the line camera 42, there is needed the first imaging data for at least 5 ms. A time required for the process of the first determination step in the computer 61 is set to 1 ms, and the instruction step is set to be performed after a delay time τ. In the instruction step, a time required for the transmission process of the trigger signal Trg in the computer 61 is set to 1 ms, and a time required for the reception process of the trigger signal Trg in the area camera 52 is set to 1 ms. Thereafter, the second imaging data over a predetermined period of time in the past is sent out from the area camera 52 receiving the trigger signal to the computer 62. A time required for sending out the second imaging data is set to 750 ms (=15 ms×50).

In the fourth embodiment, the second imaging data of the object cell is necessarily accumulated already and before erasing at a time point when the built-in memory of the area camera 52 receives the trigger signal Trg and starts to output the second imaging data. Therefore, the time T (8 ms+τ in the above operation example) from the start time point of the imaging of a certain cell by the line camera 42 to the start time point of outputting the second imaging data from the area camera 52 and the imaging available time tr have a relation of T<tr. Further, the distance L from the position P1 to the position P2 along the flow path 10, the moving speed V of the cell, and the imaging available time tr have a relation of L<V·tr.

In the embodiment, all the cells 30 flowing in the flow path 10 are imaged by the line camera 42 of the first observation apparatus 40. Then, all the cells 30 flowing in the flow path 10 are determined, by the computer 61, on whether the specific condition is satisfied, that is, whether there is a cell suspected as a specific cell, on the basis of the first imaging data which is sequentially output from the line camera 42 (first determination step).

The second imaging data of the cell 30 which is determined as suspicious as a specific cell by the computer 61 is already stored in the built-in memory of the ring buffer type of the area camera 52, and selectively output from the area camera 52. At this time, in a case where there are two or more cells 30 determined as suspicious as a specific cell by the computer 61, the second imaging data of these two or more cells 30 may be continuously output from the area camera 52. Then, the computer 62 more strictly determines whether the cell 30 is a specific cell on the basis of the second imaging data output from the area camera 52 (second determination step).

In this way, all the cells are determined on whether there is a cell suspected as a specific cell on the basis of the first imaging data of the line camera 42 which has a less amount of data transfer to the outside and does not take a time for transfer. On the other hand, only a cell suspected as a specific cell is determined on whether the cell is a specific cell on the basis of the second imaging data of the area camera 52 which has a large amount of data transfer to the outside and takes a time for transfer. Therefore, even in the fourth embodiment, it is possible to observe a large number of cells and to efficiently identify a specific cell (cancer cell).

The control device 60 in the fourth embodiment may be similarly configured to the first embodiment, or instead may be similarly configured to the second or third embodiment.

Fifth Embodiment

Figure 7:
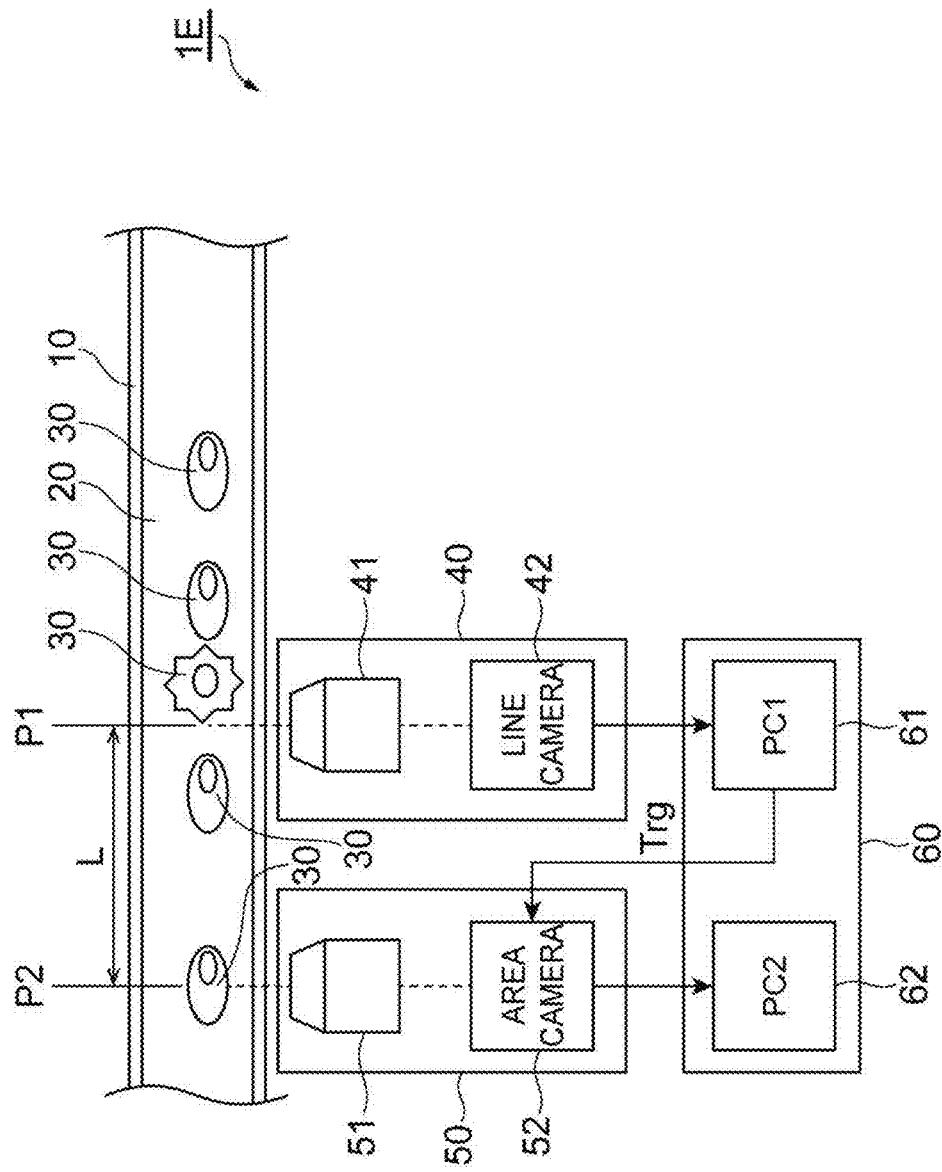
FIG. 7 is a diagram illustrating a configuration of a cell observation system 1E of a fifth embodiment.

FIG. 7 is a diagram illustrating a configuration of a cell observation system 1E of a fifth embodiment. The fifth embodiment is different from the fourth embodiment in the imaging positions of the line camera 42 and the area camera 52.

In the fourth embodiment, the position P2 of the imaging by the area camera 52 is on the downstream side from the position P1 of the imaging by the line camera 42 in the moving direction of the cell 30 in the flow path 10. In contrast, in the fifth embodiment, the position P2 of the imaging by the area camera 52 is on the upstream side from the position P1 of the imaging by the line camera 42 in the moving direction of the cell 30 in the flow path 10.

Even in the fifth embodiment, a large number of cells can be observed similarly to the fourth embodiment, and it is possible to identify a specific cell (cancer cell) with efficiency.

The control device 60 in the fifth embodiment may be similarly configured to the first embodiment, or instead may be similarly configured to the second or third embodiment.

Sixth Embodiment

Figure 8:
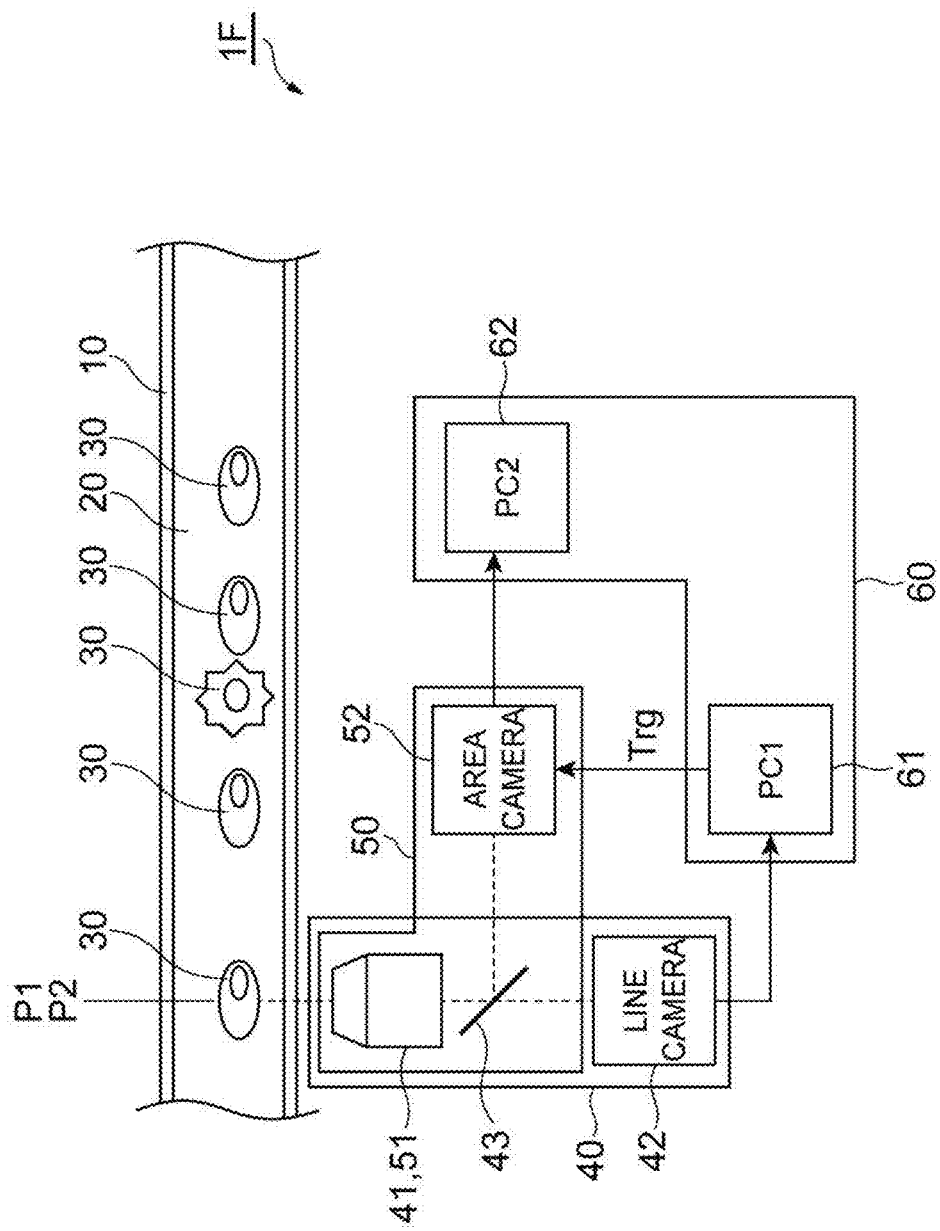
FIG. 8 is a diagram illustrating a configuration of a cell observation system 1F of a sixth embodiment.

FIG. 8 is a diagram illustrating a configuration of a cell observation system 1F of a sixth embodiment. The sixth embodiment is different from the fourth and fifth embodiments in the imaging positions of the line camera 42 and the area camera 52.

In the fourth and fifth embodiments, the position P2 of the imaging by the area camera 52 is different from the position P1 of the imaging by the line camera 42. In contrast, in the sixth embodiment, the position P2 of the imaging by the area camera 52 is the same as the position P1 of the imaging by the line camera 42 in the moving direction of the cell 30 in the flow path 10.

In the sixth embodiment, at least parts of the optical systems (first and second optical systems) of the first observation apparatus 40 and the second observation apparatus 50 may be configured in common. For example, a common lens may be employed for the objective lens 41 and the objective lens 51. In this case, the light output from the objective lens is split into two components by a beam splitter 43, one split light is received by the line camera 42, and the other split light is received by the area camera 52. In addition, a light source, a mirror, a lens, a modulator and the like may be used as optical components which can be commonly used in the first observation apparatus 40 and the second observation apparatus 50.

Even in the sixth embodiment, a large number of cells can be observed similarly to the fourth embodiment, and it is possible to identify a specific cell (cancer cell) with efficiency.

The control device 60 in the sixth embodiment may be similarly configured to the first embodiment, or instead may be similarly configured to the second or third embodiment.

Seventh Embodiment

Figure 9:
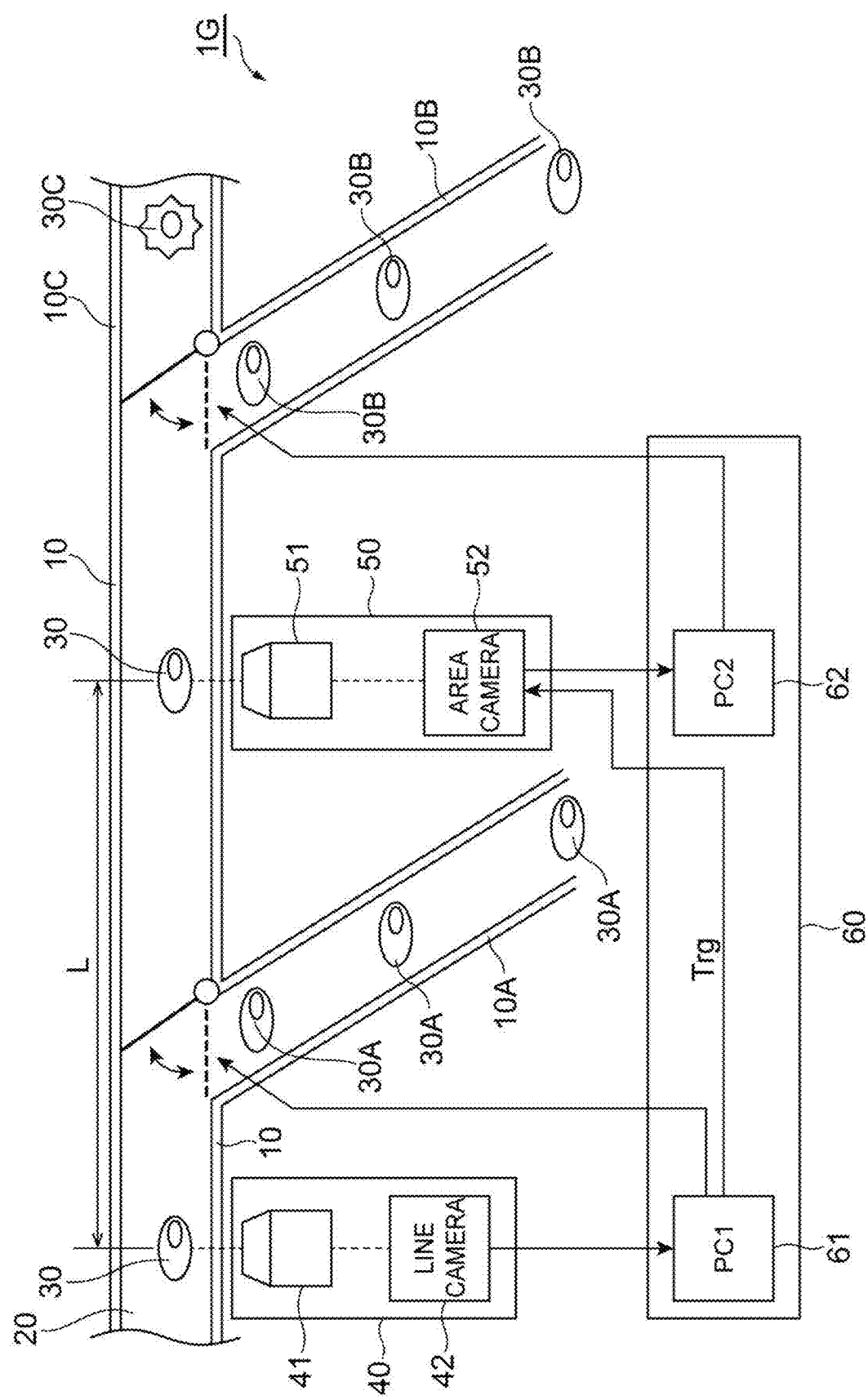
FIG. 9 is a diagram illustrating a configuration of a cell observation system 1G of a seventh embodiment.

FIG. 9 is a diagram illustrating a configuration of a cell observation system 1G of a seventh embodiment. The seventh embodiment is different from the first embodiment in that the flow path 10 is branched into branch flow paths 10A, 10B, and 10C, and in that the cell is sorted to any one of the branch flow paths 10A, 10B, and 10C according to a determination result by the control device 60.

The computer 61 inputs the first imaging data which is output from the line camera 42 of the first observation apparatus 40, and analyzes the first imaging data so as to detect a position of the cell and to determine whether the cell satisfies a specific condition (first determination step). The computer 61 outputs the trigger signal Trg to instruct the area camera 52 of the second observation apparatus 50 to output the second imaging data of the cell 30 determined to satisfy the specific condition (instruction step).

The trigger signal Trg is input to the area camera 52. Further, the computer 61 causes the cell 30 flow to a different flow path according to a determination result in the first determination step. That is, the computer 61 causes a cell 30A determined not to satisfy the specific condition to flow to the branch flow path 10A, and causes the cell 30 determined to satisfy the specific condition to flow to the flow path 10 without change.

The computer 62 inputs the second imaging data output from the area camera 52 of the second observation apparatus 50 which receives the output instruction by the trigger signal Trg, and analyzes the second imaging data so as to determine whether the cell 30 is a specific cell (second determination step). Further, the computer 62 causes the cell 30 to flow to a different flow path according to a determination result in the second determination step. That is, the computer 62 causes a cell 30B determined not a specific cell to flow to the branch flow path 10B, and causes a cell 30C determined as a specific cell to flow to the branch flow path 10C.

The cell 30A flowing in the branch flow path 10A is a cell which is determined not a specific cell in the first determination step. The cell 30B flowing in the branch flow path 10B is a cell which is determined as suspicious as a specific cell in the first determination step, but further, which is determined not a specific cell in the second determination step. The cell 30C flowing in the branch flow path 10C is a cell which is determined as a specific cell in the second determination step.

Even in the seventh embodiment, a large number of cells can be observed similarly to the first embodiment, and it is possible to identify a specific cell (cancer cell) with efficiency. Further, in the seventh embodiment, the cell can be isolated into a specific cell (cancer cell) and a non-specific cell (normal cell).

Here, even in the second to sixth embodiments, there may be provided a branch flow path to cause the cell determined as a specific cell to selectively flow.

(First Configuration Example of First Observation Apparatus 40)

Hereinbelow, a configuration example of the first observation apparatus 40 and a content of an analysis process of the imaging data will be described.

Figure 10:
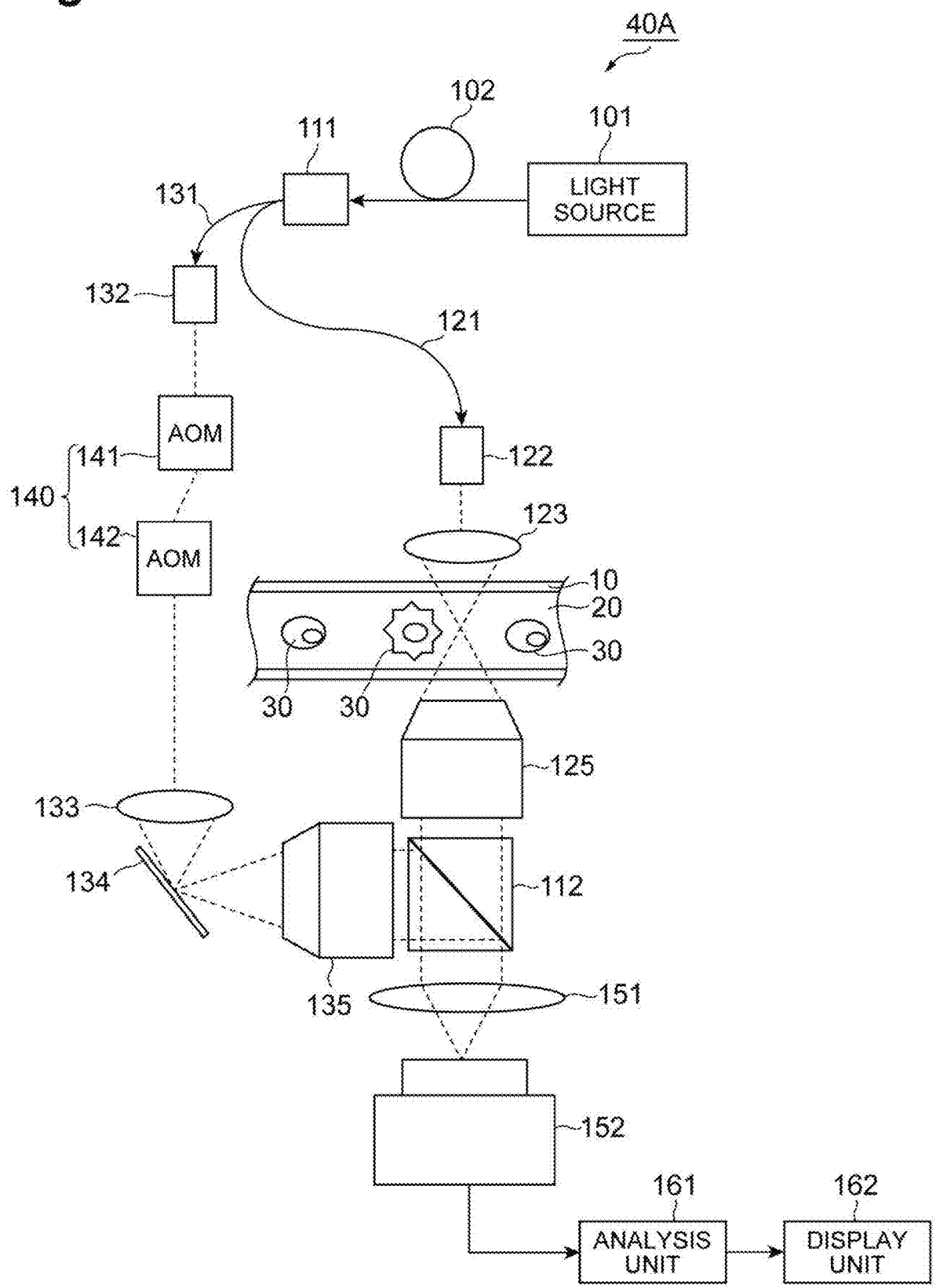
FIG. 10 is a diagram illustrating a first configuration example of a first observation apparatus 40.

FIG. 10 is a diagram illustrating a first configuration example of the first observation apparatus 40. An observation apparatus 40A of the first configuration example generates a phase image on the basis of an interference image of the cell 30 which flows in the flow path 10 with the fluid 20. For example, the flow path 10 is a flow cell, the fluid 20 is blood, and the cell 30 is a red blood cell, a white blood cell, a CTC, and the like.

The observation apparatus 40A includes a light source 101, an optical fiber 102, a splitting unit 111, a combining unit 112, an optical fiber 121, a collimator 122, a cylindrical lens 123, an objective lens 125, an optical fiber 131, a collimator 132, a cylindrical lens 133, a mirror 134, an objective lens 135, a modulation unit 140, a lens 151, and an imaging unit 152. Here, the objective lens 125 corresponds to the objective lens 41 in FIG. 1 and the like. The imaging unit 152 corresponds to the line camera 42 in FIG. 1 and the like. An analysis unit 161 and a display unit 162 in the drawing correspond to the computer 61 in FIG. 1 and the like.

The light source 101 outputs light. The light source 101 may output temporally and spatially coherent light, only the temporally coherent light, or only the spatially coherent light. Further, the light source 101 may output temporally and spatially incoherent light. The light source 101 is, for example, a laser light source, and specifically, a HeNe laser light source of 7 mW output power or the like is used.

The optical fiber 102 is used to optically couple the light source 101 and the splitting unit 111, and guides the light output from the light source 101 to the splitting unit 111. The splitting unit 111 splits the light output from the optical fiber 102 into two components, and outputs as first split light and second split light. The splitting unit 111 may be, for example, a half mirror, or may be a fiber coupler. An interference optical system from the splitting unit 111 to the combining unit 112 forms a Mach-Zehnder interferometer.

The optical fiber 121, the collimator 122, the cylindrical lens 123, and the objective lens 125 are provided on an optical path of the first split light from the splitting unit 111 to the combining unit 112. Further, the flow path 10 is disposed to be intersected with the first optical path.

The optical fiber 121 is used to optically couple the splitting unit 111 and the collimator 122, and guides the first split light output from the splitting unit 111 to the collimator 122. The collimator 122 inputs the first split light output from the optical fiber 121, and collimates the first split light to output as parallel light of a predetermined beam diameter.

The cylindrical lens 123 is a focusing optical element which performs focused irradiation of the first split light to a focusing region which is longer in a direction intersecting with a moving direction than in the moving direction of the cell 30 in the flow path 10. The cylindrical lens 123 inputs the first split light output from the collimator 122, and focuses the first split light with respect to the moving direction of the cell 30. The focusing region is a linear region intersecting with the moving direction of the cell 30 in the flow path 10. The objective lens 125 inputs the first split light transmitting the fluid 20 and the cell 30 moving in the flow path 10, and outputs the first split light to the combining unit 112.

The optical fiber 131, the collimator 132, the cylindrical lens 133, the mirror 134, and the objective lens 135 are provided on an optical path of the second split light from the splitting unit 111 to the combining unit 112. Further, acousto-optical elements 141 and 142 are also provided on the optical path of the second split light.

The optical fiber 131 is used to optically couple the splitting unit 111 and the collimator 132, and guides the second split light output from the splitting unit 111 to the collimator 132. The collimator 132 inputs the second split light output from the optical fiber 131, and collimates the second split light to output as parallel light of a predetermined beam diameter.

The cylindrical lens 133 is a focusing optical element which performs focused irradiation of the second split light to the focusing region long in one direction. The cylindrical lens 133 inputs the second split light which is output from the collimator 132 and reaches through the acousto-optical elements 141 and 142, and focuses the second split light onto a reflection surface of the mirror 134. The focusing region is a linear region long in one direction. The objective lens 135 inputs the second split light which is output from the cylindrical lens 133 and reflected on the mirror 134, and outputs the second split light to the combining unit 112.

The combining unit 112 inputs the first split light output from the objective lens 125, inputs the second split light output from the objective lens 135, combines the first split light and the second split light, and outputs the combined light to the lens 151. The combining unit 112 is, for example, a half mirror.

The collimator 132, the cylindrical lens 133, and the objective lens 135 provided on the optical path of the second split light are preferably the same as the collimator 122, the cylindrical lens 123, and the objective lens 125 provided on the optical path of the first split light. With such a configuration, even in a case where the light source 101 outputs temporally incoherent light, the interference between the first split light and the second split light combined by the combining unit 112 can be increased.

As a focusing optical element which focuses light to a linear region long in one direction, a Fresnel biprism, a Fresnel zone plate, an axicon lens, a holographic optical element, and a spatial light modulator may be used besides the cylindrical lens.

The modulation unit 140 includes the acousto-optical elements 141 and 142, and temporally changes a phase difference between the first split light and the second split light at the combining by the combining unit 112. The acousto-optical element 141 of the former stage inputs a sinusoidal electric signal of a frequency $\Omega_0$ to form a diffraction grating, inputs the second split light output from the collimator 132, and diffracts the second split light by the diffraction grating to output +1 order diffracted light. The acousto-optical element 142 of the latter stage inputs a sinusoidal electric signal of a frequency $(\Omega_0+\Omega)$ to form a diffraction grating, inputs the +1 order diffracted light of the second split light output from the acousto-optical element 141, and diffracts the second split light by the diffraction grating to output −1 order diffracted light.

The −1 order diffracted light of the second split light output from the acousto-optical element 142 has an optical frequency which is shifted by the frequency $\Omega$ with respect to an optical frequency of the first split light. For example, $\Omega_0$ is 200 MHz, and $\Omega$ is 20 kHz.

Even when the acousto-optical element 141 outputs the −1 order diffracted light, and the acousto-optical element 142 outputs the +1 order diffracted light, the +1 order diffracted light of the second split light output from the acousto-optical element 142 similarly can have the optical frequency shifted by the frequency $\Omega$ with respect to the optical frequency of the first split light.

In this way, the modulation unit 140 including the acousto-optical elements 141 and 142 sets the optical frequency to be different by $\Omega$ between the first split light and the second split light at the combining by the combining unit 112, and therefore, the phase difference between the first split light and the second split light can be temporally changed by the frequency $\Omega$.

Here, the acousto-optical elements 141 and 142 may be provided on the optical path of the first split light, or one element may be provided on the optical path of the first split light and the other element on the optical path of the second split light. The modulation unit which temporally changes the phase difference between the first split light and the second split light at the combining by the combining unit 112 is not limited to the configuration in which the acousto-optical element is included.

The lens 151 inputs the combined light output from the combining unit 112, and causes the combined light to be incident on a light receiving plane of the imaging unit 152. The cell 30 in the flow path 10 and the light receiving plane of the imaging unit 152 are in an imaging relation by the objective lens 125 and the lens 151 on the optical path therebetween.

The imaging unit 152 is a photodetector which includes a plurality of pixels arranged in a direction intersecting with the moving direction of an image of the cell 30 on the light receiving plane. On the light receiving plane, an imaging region on which the linear focusing region by the cylindrical lens 123 is imaged is a region long in a predetermined direction, and the plurality of pixels are arranged along the predetermined direction in the imaging region. The imaging unit 152 receives the combined light which is output from the combining unit 112 and arrives through the lens 151, and repeatedly outputs a detection signal indicating a one-dimensional interference image at a predetermined line rate.

The imaging unit 152 is, for example, a line sensor in which a plurality of pixels are disposed one-dimensionally. Further, the imaging unit 152 may be a two-dimensional sensor which is configured to read any one line of pixels arranged in a direction intersecting with the moving direction of the image of the cell 30 on the light receiving plane. Hereinbelow, the description will be given assuming that the imaging unit 152 is a line sensor, however, in a case where the imaging unit 152 is a two-dimensional sensor, the above-described one-line pixels will be considered as a line sensor.

The analysis unit 161 inputs the detection signal output repeatedly from the imaging unit 152, and generates a two-dimensional image on the basis of the one-dimensional interference image at each time point indicated by the detection signal. The analysis unit 161 generates, for example, a two-dimensional phase image of the cell 30 as the two-dimensional image by a phase retrieval method (see Non Patent Documents 1 to 3) on the basis of the one-dimensional interference image at each time point.

Examples of the phase retrieval method include a phase shift method, a Fourier transform method, and a Hilbert transform method. Further, for example, the analysis unit 161 generates the two-dimensional interference image on the basis of a plurality of one-dimensional interference images at a plurality of time points.

In order for the analysis unit 161 to generate the phase image with a high accuracy on the basis of the interference image, the frequency $\Omega$ of the phase difference change by the modulation unit 140 (the acousto-optical elements 141 and 142) is preferably ⅓ times the line rate of the imaging unit 152 or less. Further, the frequency $\Omega$ is preferably ¼ times the line rate.

The analysis unit 161 analyzes a shape (an external form, a shape of a nucleus, or the like) of the cell 30 on the basis of the two-dimensional phase image to determine whether the cell 30 is the CTC. Further, the analysis unit 161 preferably performs a correction process in order to reduce a temporal or spatial influence of noises in the phase image.

For example, the analysis unit 161 may be configured by a general-purpose computer. The computer is configured by a CPU (central processing unit) which is a processor, a RAM (random access memory) or a ROM (read only memory) which is a recording medium, an input unit such as a keyboard and a mouse, and an input-output module. The computer reads a program and the like on hardware such as the CPU and the RAM, causes the CPU to perform generation of the phase image on the basis of the detection signal from the imaging unit 152 and the like, and reads and writes the data in the RAM.

Further, the analysis unit 161 may be configured by a dedicated device using, for example, a microcomputer and an FPGA (field programmable gate array). In a case where a dedicated device is used, the analysis unit 161 can generate and analyze the phase image at a high speed, and for example, the analysis unit can both input the detection signal from the imaging unit 152 and generate the phase image on the basis of the input detection signal in parallel in real time.

The display unit 162 is, for example, a display, which displays the interference image and the phase image generated by the analysis unit 161, and displays an analysis result on the basis of the phase image by the analysis unit 161. When the analysis unit 161 determines that the cell 30 is the CTC, the display unit 162 may make a sound or emit light to display the fact.

Next, the operation of the observation apparatus 40A of the first configuration example will be described, and a processing content of the analysis unit 161 will be described.

The light output from the light source 101 is guided by the optical fiber 102 to the splitting unit 111, and split by the splitting unit 111 to be the first split light and the second split light.

The first split light output from the splitting unit 111 is guided by the optical fiber 121 to the collimator 122, and output as parallel light of a predetermined beam diameter from the collimator 122. The first split light output from the collimator 122 is focused and incident by the cylindrical lens 123 onto the focusing region which is long in a direction intersecting with the moving direction of the cell 30 in the flow path 10. The first split light which has transmitted the fluid 20 and the cell 30 is input to the combining unit 112 through the objective lens 125.

The second split light output from the splitting unit 111 is guided by the optical fiber 131 to the collimator 132, and output as parallel light of a predetermined beam diameter from the collimator 132. The second split light output from the collimator 132 is shifted by an optical frequency $\Omega$ by the modulation unit 140, and focused to the focusing region which is long in one direction by the cylindrical lens 133. Further, the second split light is input to the combining unit 112 through the objective lens 135.

The first split light output from the objective lens 125 and the second split light output from the objective lens 135 are combined by the combining unit 112. The combined light output from the combining unit 112 is received by the imaging unit 152 through the lens 151. The detection signal indicating the one-dimensional interference image is repeatedly output at a predetermined line rate from the imaging unit 152.

The detection signal repeatedly output from the imaging unit 152 is input to the analysis unit 161. In the analysis unit 161, the two-dimensional phase image of the cell 30 is generated by the phase retrieval method on the basis of the one-dimensional interference image at each time point indicated by the detection signal. Further, the analysis unit 161 performs the correction process for reducing a temporal or spatial influence of noises in the phase image.

An example of a method for the analysis unit 161 to generate the phase image by the phase retrieval method from the interference image is as follows. The detection signal output from the imaging unit 152 is denoted by $I(x_i, t)$. $x_i$ represents a position (pixel number i) in an arranging direction of the plurality of pixels in the light receiving plane of the imaging unit 152, and also represents a position in a direction intersecting with the moving direction of the cell 30 in the flow path 10. t represents a time point when the detection signal is output from the imaging unit 152, and also represents a position in the moving direction of the cell 30 in the flow path 10. Therefore, a detection signal $I(x_i, t)$ repeatedly output from the imaging unit 152 at a predetermined line rate represents a two-dimensional interference image. Therefore, the two-dimensional phase image can be generated by the phase retrieval method on the basis of the two-dimensional interference image.

For example, in a case where the phase shift method is used in the phase retrieval method and a line rate $f_{line}$ of the imaging unit 152 is four times the optical frequency shift amount (a reciprocal of the period of a temporal change of the phase difference) $\Omega$, a two-dimensional phase image $\phi(x_i, t)$ can be generated by the following Formula (1a) and Formula (1b). $t_1$ to $t_4$ represent time points different from each other in the period when the cell 30 seems to be stopped, and satisfy $t_1 < t_2 < t_3 < t_4$. t represents a time point (for example, $t=(t_1+t_4)/2$) representing the period. j represents an imaginary unit.

$$\phi(x,t) = \arg(Z) \tag{1a}$$

$$z(x_i,t) = [I(x_i,t_1) - I(x_i,t_3)] + j[I(x_i,t_2) - I(x_i,t_4)] \tag{1b}$$

When an arrangement pitch of the pixels intersecting with the moving direction of the image of the cell 30 on the light receiving plane of the imaging unit 152 is set to p, and a magnification when the cell 30 is imaged onto the light receiving plane of the imaging unit 152 is set to M, a resolution $r_x$ in the arrangement direction of the pixels on the light receiving plane of the imaging unit 152 is represented by the following Formula (2). Further, when a moving speed of the cell 30 in the flow path 10 is set to V, and the line rate of the imaging unit 152 is set to $f_{line}$, a resolution $r_y$ of the moving direction of the image on the light receiving plane of the imaging unit 152 is represented by the following Formula (3). In order to set the resolutions to be equal in the x direction and the y direction in the two-dimensional phase image, the imaging unit 152 may operate at the line rate of $f_{line}$ defined in the following Formula (4).

$$r_x = \frac{p}{M} \tag{2}$$

$$r_y = \frac{V}{f_{line}} \tag{3}$$

$$f_{line} = \frac{MV}{p} \tag{4}$$

A method of correcting the phase image in the analysis unit 161 is as follows. In general, a phase image $\phi(x, t)$ generated on the basis of the interference image is defined by the following Formula (5). $\Phi(x, t)$ represents an actual phase image. $\phi_s(x)$ represents phase data of a fixed pattern of a background. $\phi_{dev}(t)$ represents phase data of a temporal variation of an offset value.

$$\phi(x,t) = \Phi(x,t) + (x) + \phi_s(x) + \phi_{dev}(t) \tag{5}$$

$\phi_s(x)$ indicates that spatial noises are overlapped with the actual phase image $\Phi(x, t)$, and is caused by a distortion of an optical wavefront due to the optical system and the flow path. With regard to $\phi_s(x)$, for example, the interference image in a state where the cell 30 does not flow in the flow path 10, or the interference image of a region without the cell 30 in a state where the cell 30 flows is acquired, and the phase image may be generated on the basis of the interference image. The phase image generated as described above becomes $\phi_s(x)$.

Figure 11A:
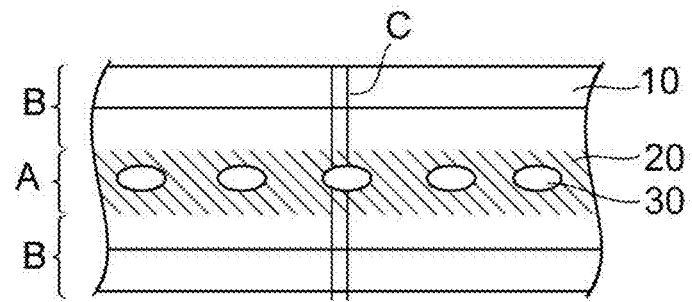
FIG. 11A and FIG. 11B are diagrams for describing a flow path 10, and (A) a diagram when viewed in a direction of an optical axis of an objective lens 125, and (B) a diagram when viewed in a direction perpendicular to the optical axis of the objective lens 125.
Figure 11B:
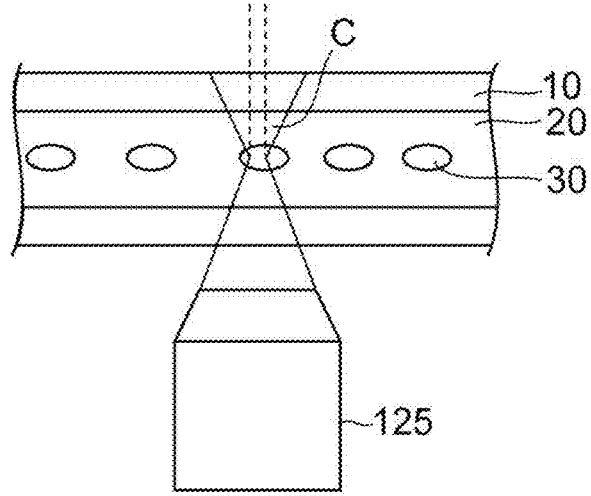

$\phi_{dev}(t)$ indicates that temporal noises are overlapped with the actual phase image $\Phi(x, t)$, and is caused by a vibration due to disturbance noises to the optical system. As illustrated in FIG. 11A and FIG. 11B, there are reference regions B in the flow path 10 in which the cell 30 does not pass through on both sides of a measurement region A in which the cell 30 passes through, and therefore, $\phi_{dev}(t)$ can be obtained as a temporal variation component which is obtained from the phase image of the reference region B in the phase image $\phi(x, t)$. FIG. 11A is a diagram when viewed in a direction of the optical axis of the objective lens 125, and FIG. 11B is a diagram when viewed in a direction perpendicular to the optical axis of the objective lens 125. Further, in these drawings, a focusing state of the first split light C by the cylindrical lens 123 is also illustrated.

The analysis unit 161 performs the correction process of subtracting $\phi_s(x)$ and $\phi_{dev}(t)$ from the phase image $\phi(x, t)$ which is generated on the basis of the interference image, and performs a phase unwrapping process, so that the actual phase image $\Phi(x, t)$ can be obtained. Further, it is possible to obtain a phase image improved in an SN ratio even by subtracting any one of $\phi_s(x)$ and $\phi_{dev}(t)$ from the phase image $\phi(x, t)$.

The analysis unit 161 can perform a fixed pattern subtraction (subtraction of $\phi_s(x)$), an offset subtraction (subtraction of $\phi_{dev}(t)$), and a phase unwrapping in an arbitrary order, and can achieve the same result in any case. That is, any one of the following six orders may be used.

(A) "Phase unwrapping"⇒"Fixed pattern subtraction"⇒"Offset subtraction"

(B) "Phase unwrapping"⇒"Offset subtraction"⇒"Fixed pattern subtraction"

(C) "Fixed pattern subtraction"⇒"Phase unwrapping"⇒"Offset subtraction"

(D) "Fixed pattern subtraction"⇒"Offset subtraction"⇒"Phase unwrapping"

(E) "Offset subtraction"⇒"Phase unwrapping"⇒"Fixed pattern subtraction"

(F) "Offset subtraction"⇒"Fixed pattern subtraction"⇒"Phase unwrapping"

Here, in any case, in the fixed pattern subtraction performed after the phase unwrapping, there is a need to use $\phi_s(x)$ which has been phase unwrapped in advance. Further, in the offset subtraction performed after the phase unwrapping, there is a need to use $\phi_{dev}(t)$ which has been phase unwrapped in advance.

On the other hand, in the fixed pattern subtraction and the offset subtraction performed before the phase unwrapping, the phase value obtained as a result of these processes may deviate from a predetermined range (for example, $-\pi \leq \phi < \pi$) of $2\pi$ width. For example, assuming $\phi(x, t)=-2$ (radian), $\phi_s(x)=-1$ (radian), and $\phi_{dev}(t)=-1$ (radian), $\Phi(x, t)=-4$ (radian) is obtained as a result of the correction process, and deviated from the range of $-\pi \leq \phi < \pi$. In that case, by using a modulo operator, the result of the correction process can be kept to fall within the range of $-\pi \leq \phi < \pi$.

In order to perform the correction process while keeping the phase range in $-\pi \leq \phi < \pi$, the fixed pattern subtraction and the offset subtraction may be performed by division in a complex domain. That is, when a phase $\phi_2$ is subtracted from a phase $\phi_1$, as defined in the following Formula (6a) and Formula (6b), a complex number $C_1$ of which the absolute value is 1 and the phase is $\phi_1$, and a complex number $C_2$ of which the absolute value is 1 and the phase is $\phi_2$ are assumed. When dividing by the complex number $C_2$, the complex number $C_1$ becomes as the following Formula (7). Then, as a phase as a result of the division, a value obtained by subtracting the phase $\phi_2$ from the phase $\phi_1$ can be uniquely obtained as defined in the following Formula (8).

$$C_1 = \cos\phi_1 + j \cdot \sin\phi_1 = \exp(j \cdot \phi_1) \quad (6a)$$

$$C_2 = \cos\phi_2 + j \cdot \sin\phi_2 = \exp(j \cdot \phi_2) \quad (6b)$$

$$\frac{C_1}{C_2} = \frac{\cos\phi_1 + j \cdot \sin\phi_1}{\cos\phi_2 + j \cdot \sin\phi_2} = \frac{\exp(j \cdot \phi_1)}{\exp(j \cdot \phi_2)} = \exp(j \cdot (\phi_1 - \phi_2)) \quad (7)$$

$$\arg\left(\frac{C_1}{C_2}\right) = \phi_1 - \phi_2 \quad (8)$$

Similarly, when the correction process of the following Formula (9) is performed, complex numbers $C(x, t)$, $C_s(x)$, and $C_{dev}(t)$ defined in the following Formula (10a), Formula (10b), and Formula (10c) are assumed for $\phi(x, t)$, $\phi_s(x)$, and $\phi_{dev}(t)$ respectively. As a result, the actual phase image $\Phi(x, t)$ before the phase unwrapping can be uniquely obtained from the following Formula (11).

$$\Phi(x, t) = \phi(x, t) - \phi_s(x) - \phi_{dev}(t) \quad (9)$$

$$C(x, t) = \exp(j \cdot \phi(x, t)) \quad (10a)$$

$$C_s(x) = \exp(j \cdot \phi_s(x)) \quad (10b)$$

$$C_{dev}(t) = \exp(j \cdot \phi_{dev}(t)) \quad (10c)$$

$$\Phi(x, t) = \arg\left(\frac{C(x, t)}{C_s(x) \cdot C_{dev}(t)}\right) \quad (11)$$

In this way, as an advantage of subtracting the phases by the division in the complex domain, in a case where the original data of the phase calculation is given as a complex number having an argument of the phase, instead of the phase, the number of calculation steps can be reduced, and the calculation can be performed at a high speed. For example, in the case of the phase shift method of four points as defined in Formula (1a) and Formula (1b), $\phi$ is expressed as the argument of $Z(x, t)$ of Formula (1b). When an electronic computer is used, the calculation of the argument, that is, arc tangent, takes a long time. However, when the phase value is used for the first time immediately before the phase unwrapping while the obtained phase data is used as the complex number itself, the time-consuming calculation of the arc tangent can be completed at a time, and the calculation can be performed at a high speed by Formula (11).

As a procedure of obtaining the actual phase image $\Phi(x, t)$, the procedure easy for intuitive understanding is the procedure (A) ("Phase unwrapping"⇒"Fixed pattern subtraction"⇒"Offset subtraction") in which the phase unwrapping is performed first. The procedure easy for the electronic calculator is the procedure (F) ("Offset subtraction"⇒"Fixed pattern subtraction"⇒"Phase unwrapping") in which the calculation of the argument and the phase unwrapping are performed last.

FIG. 12 to FIG. 15 are diagrams illustrating an example of the phase image. Herein, the respective processes of the offset subtraction, the fixed pattern subtraction, and the phase unwrapping are performed in this order on the phase image (original phase image) generated on the basis of the interference image, and the corrected phase image after the phase unwrapping is generated. In these drawings, the horizontal direction represents time, and the vertical direction represents position in the width direction of the flow path 10. The fluid 20 is blood, and there is the CTC as the cell 30 near the center of the respective drawings.

Figure 12:
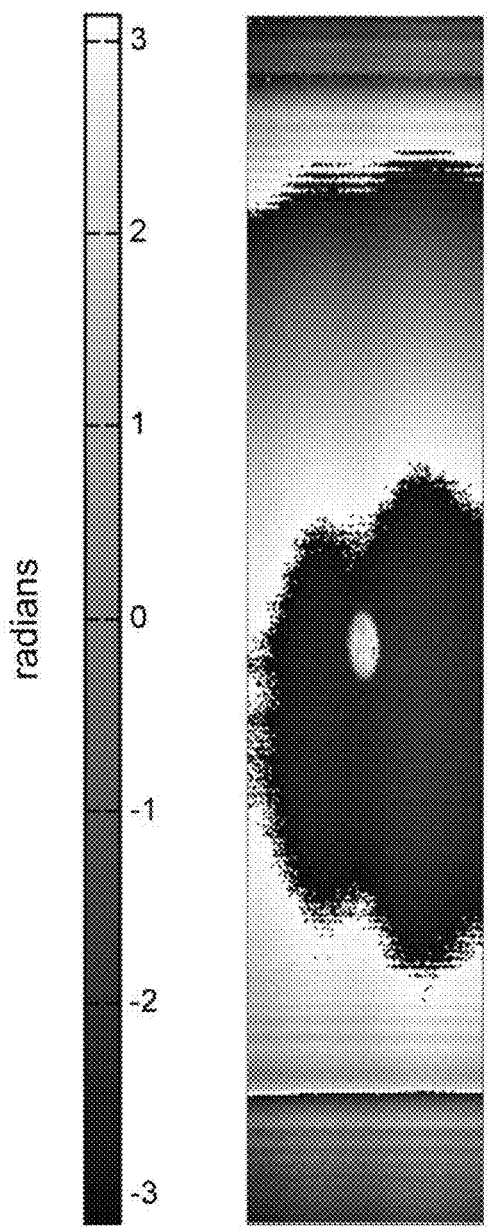
FIG. 12 is a diagram illustrating a phase image (original phase image $\phi(x, t)$) before correction.

FIG. 12 is a diagram illustrating the phase image (original phase image $\phi(x, t)$) before correction. In the phase image $\phi(x, t)$, the temporal noise and the spatial noise are overlapped with the actual phase image $\Phi(x, t)$ (Formula (5)), which corresponds to $\arg(C(x, t))$ when being expressed by the complex domain as defined in Formula (10a), Formula (10b), and Formula (10c).

Figure 13:
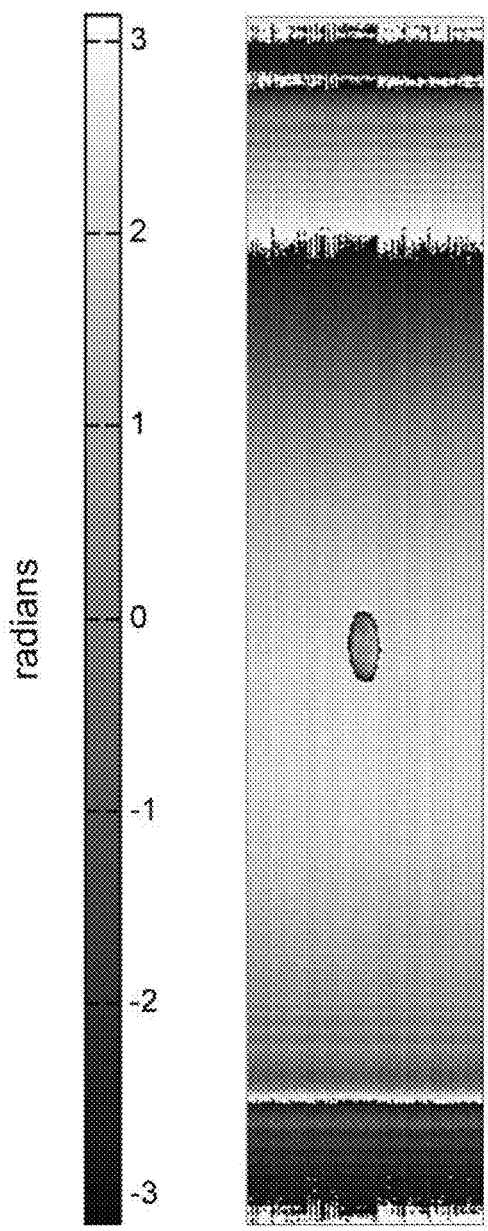
FIG. 13 is a diagram illustrating a phase image after an offset subtraction.

FIG. 13 is a diagram illustrating a phase image ($\phi(x, t)-\phi_{dev}(t)$) after an offset subtraction. The phase image is obtained by subtracting the temporal noise from the original phase image $\phi(x, t)$, which corresponds to $\arg(C(x, t)/C_{dev}(t))$ when being expressed by the complex domain.

Figure 14:
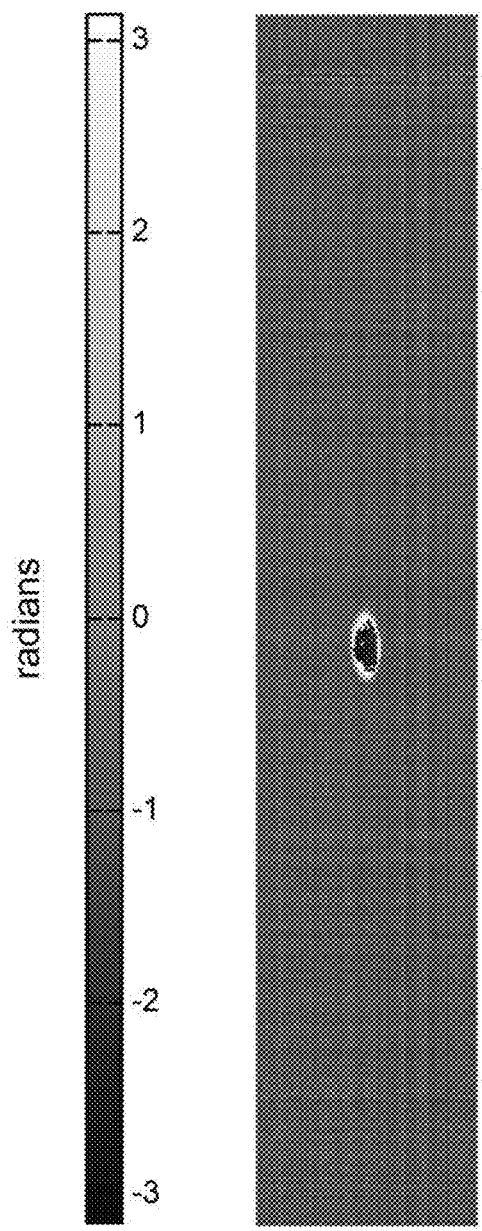
FIG. 14 is a diagram illustrating a phase image after a fixed pattern subtraction.

FIG. 14 is a diagram illustrating a phase image ($\phi(x, t)-\phi_{dev}(t)-\phi_s(x)$) after a fixed pattern subtraction. The phase image is obtained by subtracting the temporal noise and the spatial noise from the original phase image $\phi(x, t)$, which corresponds to Formula (11) when being expressed by the complex domain. The phase image corresponds to the actual phase image $\Phi(x, t)$ before the phase unwrapping.

Figure 15:
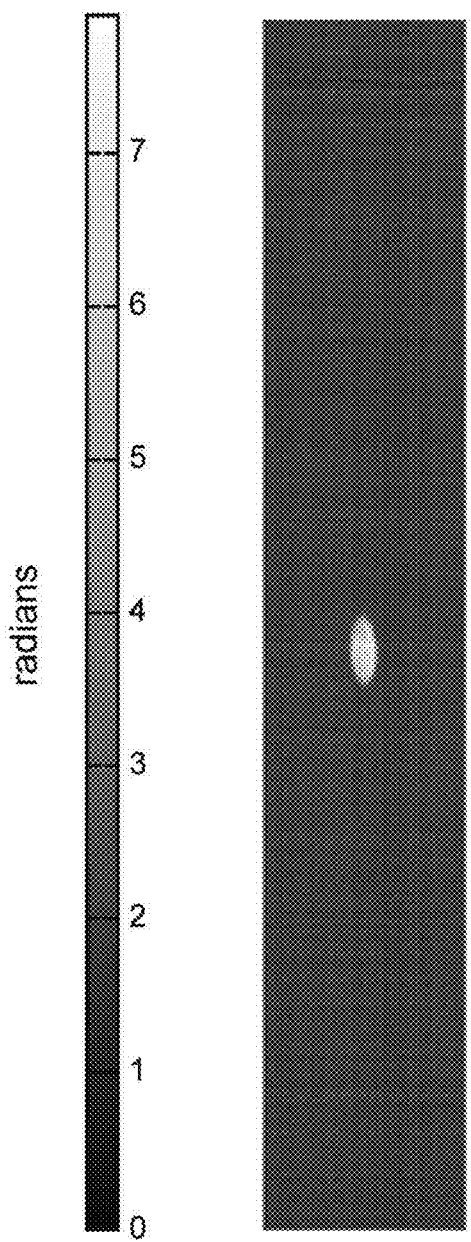
FIG. 15 is a diagram illustrating an actual phase image $\Phi(x, t)$ after phase unwrapping.

FIG. 15 is a diagram illustrating the actual phase image $\Phi(x, t)$ after the phase unwrapping. As can be seen from these drawings, the shape of the cell 30 can be recognized even in the original phase image (FIG. 12), however, the shape of the cell 30 can be clearly recognized in the phase image (FIG. 13) after the offset subtraction and the phase image (FIG. 14) after the fixed pattern subtraction, and further, in the actual phase image (FIG. 15) after the phase unwrapping, the shape of the cell 30 can be more clearly recognized.

As described above, in the present embodiment, the two-dimensional phase image of the cell 30 is generated by the analysis unit 161 on the basis of the detection signal output from the imaging unit 152, using the imaging unit 152 which receives the combined light and repeatedly outputs the detection signal indicating the one-dimensional interference image, and with this configuration, it is possible to easily generate an excellent phase image of the cell 30 which flows in the flow path 10 with the fluid 20.

Further, the first split light is focused and incident on the focusing region which is long in a direction intersecting with the moving direction of the cell 30 in the flow path 10 using the focusing optical element (for example, the cylindrical lens) disposed on the optical path of the first split light, and with this configuration, the light emitted to other than the observation line is reduced while increasing the intensity of the first split light, so that it is possible to suppress stray light, and it is possible to obtain the phase image with high accuracy. Further, it is possible to obtain the phase image with high accuracy by performing the correction to reduce the spatial noises from the two-dimensional phase image or the correction to reduce the temporal noises from the two-dimensional phase image.

(Second Configuration Example of First Observation Apparatus 40)

Figure 16:
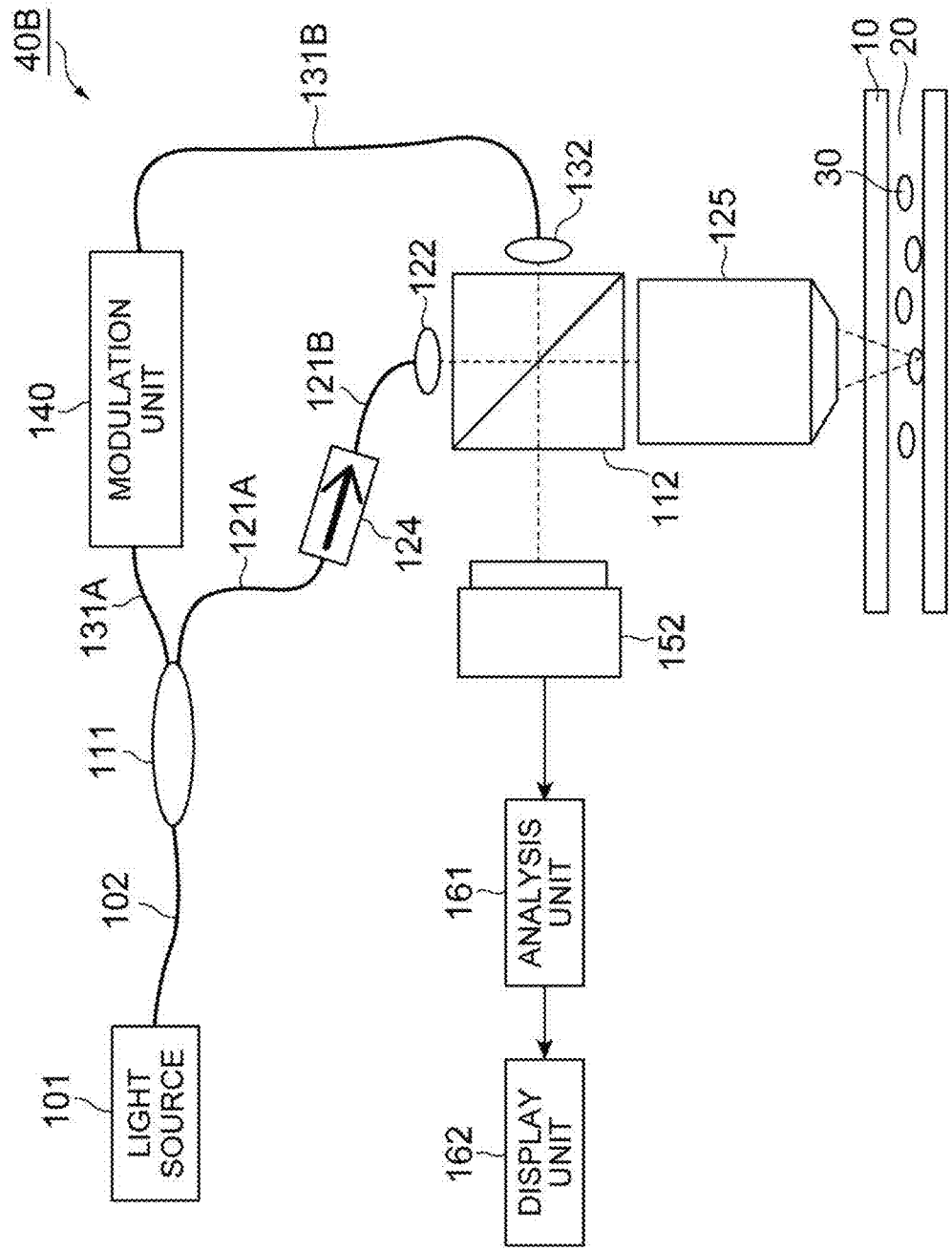
FIG. 16 is a diagram illustrating a second configuration example of the first observation apparatus 40.

FIG. 16 is a diagram illustrating a second configuration example of the first observation apparatus 40. The second configuration example is a modification of the first configuration example. An observation apparatus 40B of the second configuration example includes the light source 101, the optical fiber 102, the splitting unit 111, the combining unit 112, optical fibers 121A and 121B, the collimator 122, an optical isolator 124, the objective lens 125, optical fibers 131A and 131B, the collimator 132, the modulation unit 140, the imaging unit 152, the analysis unit 161, and the display unit 162.

In the present embodiment, the light output from the light source 101 is guided by the optical fiber 102 to the splitting unit 111, and split by the splitting unit 111 to be the first split light and the second split light.

The first split light output from the splitting unit 111 is guided by the optical fiber 121A to the optical isolator 124. The optical isolator 124 passes the light in a forward direction from the optical fiber 121A to the optical fiber 121B, but not passes the light in a reverse direction. The first split light passed through the optical isolator 124 is guided by the optical fiber 121B to the collimator 122, and is output from the collimator 122 to the combining unit 112 as parallel light of a predetermined beam diameter.

The light passed through the combining unit 112 in the first split light which is output from the collimator 122 and input to the combining unit 112 is focused and incident on the cell 30 in the flow path 10 by the objective lens 125. The bottom surface of the flow path 10 serves as a reflection surface. The first split light which is reflected on the reflection surface and input to the objective lens 125 is output from the objective lens 125 to the combining unit 112.

The second split light output from the splitting unit 111 is guided by the optical fiber 131A to the modulation unit 140. The modulation unit 140 shifts the optical frequency of the second split light by Ω. The second split light output from the modulation unit 140 is guided by the optical fiber 131B to the collimator 132, and is output from the collimator 132 to the combining unit 112 as parallel light of a predetermined beam diameter.

The first split light output from the objective lens 125 and the second split light output from the collimator 132 are combined by the combining unit 112. The combined light output from the combining unit 112 is received by the imaging unit 152. The detection signal indicating the one-dimensional interference image is repeatedly output at a predetermined line rate from the imaging unit 152.

The detection signal repeatedly output from the imaging unit 152 is input to the analysis unit 161. In the analysis unit 161, the two-dimensional phase image of the cell 30 is generated by the phase retrieval method on the basis of the one-dimensional interference image at each time point indicated by the detection signal. Further, the analysis unit 161 performs the correction process in order to reduce a temporal or spatial influence of noises in the phase image.

Here, part of the second split light output from the collimator 132 is reflected by the combining unit 112 and input to the collimator 122, but is blocked by the optical isolator 124, and thus is suppressed from returning to the light source 101.

In the present embodiment, only the first split light in the first split light and the second split light is propagated between the combining unit 112 and the flow path 10. The cylindrical lens is inserted in the middle of the optical path of the first split light therebetween, so that the first split light is focused and incident on the focusing region which is long in a direction intersecting with the moving direction of the cell 30 in the flow path 10.

Even in the second configuration example, similarly to the case of the first configuration example, it is possible to easily generate an excellent phase image of the cell 30 which flows in the flow path 10 with the fluid 20.

(Third Configuration Example of First Observation Apparatus 40)

Figure 17:
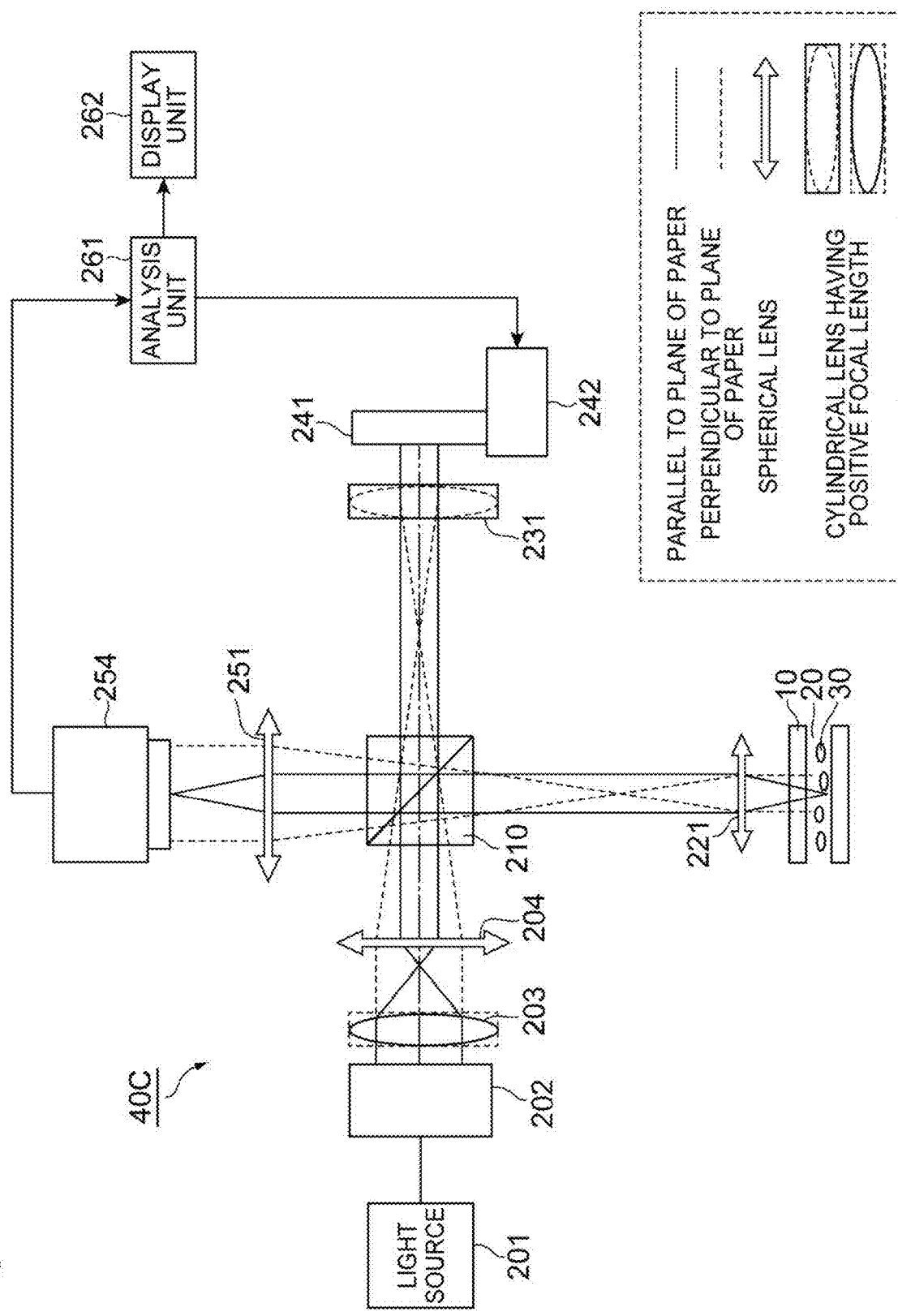
FIG. 17 is a diagram illustrating a third configuration example of the first observation apparatus 40.

FIG. 17 is a diagram illustrating a third configuration example of the first observation apparatus 40. An observation apparatus 40C of the third configuration example generates the phase image on the basis of the interference image of the cell 30 which flows in the flow path 10 with the fluid 20. For example, the flow path 10 is a flow cell, the fluid 20 is blood, and the cell 30 is a red blood cell, a white blood cell, a CTC, and the like.

The observation apparatus 40C includes a light source 201, a collimator 202, a cylindrical lens 203, a spherical lens 204, a splitting-combining unit 210, a spherical lens 221, a cylindrical lens 231, a mirror 241, a linear motion stage 242, a spherical lens 251, and an imaging unit 254. Here, the spherical lens 251 corresponds to the objective lens 41 in FIG. 1 and the like. The imaging unit 254 corresponds to the line camera 42 in FIG. 1 and the like. An analysis unit 261 and a display unit 262 in the drawing correspond to the computer 61 in FIG. 1 and the like. In the drawing, a change of a light beam width in a direction parallel to the plane of paper is depicted with a solid line, and a change of the light beam width in a direction perpendicular to the plane of paper is depicted with a dashed line.

The light source 201 outputs light. The light source 201 may output temporally and spatially coherent light, only the temporally coherent light, or only the spatially coherent light. Further, the light source 201 may output temporally and spatially incoherent light. The light source 201 is, for example, a laser light source, and specifically, a HeNe laser light source of 7 mW output power or the like is used.

The collimator 202 collimates the light output from the light source 201 to output as parallel light of a predetermined beam diameter.

The cylindrical lens 203 is a convex lens having a positive focal length. The cylindrical lens 203 inputs the light output from the collimator 202, and converges the light in the direction parallel to the plane of paper.

The spherical lens 204 inputs the light output from the cylindrical lens 203, outputs the light as parallel light in the direction parallel to the plane of paper, and converges the light in the direction perpendicular to the plane of paper.

The splitting-combining unit 210 inputs the light which is output from the light source 201 and arrives through the collimator 202, the cylindrical lens 203, and the spherical lens 204, and then, splits the input light into the first split light and the second split light, outputs the first split light to the flow path 10, and outputs the second split light to the mirror 241. Further, the splitting-combining unit 210 inputs the first split light which is reflected on the bottom surface of the flow path 10 and arrives, inputs the second split light which is reflected on the mirror 241 and arrives, combines the first split light and the second split light, and outputs the combined light to the imaging unit 254. The splitting-combining unit 210 serves as the splitting unit and the combining unit. An optical system of the first split light between the splitting-combining unit 210 and the flow path 10 and the like, and an optical system of the second split light between the splitting-combining unit 210 and the mirror 241 form a Michelson interferometer.

The spherical lens 221 is an objective lens which is provided on the optical path of the first split light between the splitting-combining unit 210 and the flow path 10. The spherical lens 221 inputs the first split light output from the splitting-combining unit 210, converges the first split light in the direction parallel to the plane of paper, outputs the first split light as parallel light in the direction perpendicular to the plane of paper, and outputs the first split light to the flow path 10. The spherical lens 221 inputs the first split light which is reflected on the bottom surface of the flow path 10, and outputs the first split light to the splitting-combining unit 210.

The cylindrical lens 231 is provided on the optical path of the second split light between the splitting-combining unit 210 and the mirror 241. The cylindrical lens 231 is a convex lens having a positive focal length. The cylindrical lens 231 inputs the second split light output from the splitting-combining unit 210, and outputs the second split light as parallel light to the mirror 241. The cylindrical lens 231 inputs the second split light which is reflected on the mirror 241, and outputs the second split light to the splitting-combining unit 210.

The linear motion stage 242 moves the mirror 241 in a direction perpendicular to a reflection surface of the mirror 241. Since a Doppler shift occurs due to the movement of the mirror 241, the linear motion stage 242 shifts the optical frequency of the second split light. That is, the linear motion stage 242 is used as a modulation unit which temporally changes the phase difference by the frequency $\Omega$ between the first split light and the second split light at the combining by the splitting-combining unit 210.

When a moving speed of the mirror 241 is set to V, and a light wavelength is set to $\lambda$, a Doppler shift amount $\Omega$ is defined by the following Formula (12). For example, in a case where the light wavelength $\lambda$ output from the light source 201 is set to 0.633 μM, and 20 kHz is to be obtained as the Doppler shift amount $\Omega$, the mirror 241 may be moved at a constant speed V of about 15.8 mm/s by the linear motion stage 242.

$$\Omega = \frac{2V}{\lambda} \tag{12}$$

Here, as a method of shifting the optical frequency of the second split light by the Doppler shift, a disk having a gradient d (radian) formed along the circumference of a radius r may be rotated around the center position of the circle at an angular velocity co, and the second split light may be entered on the periphery of the circle to be reflected. In this case, the optical frequency shift amount $\Omega$ of the second split light is defined by the following Formula (13).

$$\Omega = \frac{2r \cdot \omega \cdot \tan(d)}{\lambda} \tag{13}$$

The splitting-combining unit 210 inputs the first split light arriving from the spherical lens 221, inputs the second split light arriving from the cylindrical lens 231, and combines the first split light and the second split light to output the combined light to the spherical lens 251.

The spherical lens 251 inputs the combined light output from the splitting-combining unit 210, converges the combined light in the direction parallel to the plane of paper, and the combined light is entered on a light receiving plane of the imaging unit 254 using the combined light as parallel light in the direction perpendicular to the plane of paper. The cell 30 in the flow path 10 and the light receiving plane of the imaging unit 254 are in an imaging relation by the spherical lens 221 and the spherical lens 251 which are on the optical path therebetween.

The imaging unit 254 is a photodetector which includes a plurality of pixels arranged in a direction intersecting with the moving direction of the image of the cell 30 on the light receiving plane. On the light receiving plane, an imaging region on which the linear focusing region is formed is a region long in a predetermined direction, and the plurality of pixels are arranged along the predetermined direction in the imaging region. The imaging unit 254 receives the combined light which is output from the splitting-combining unit 210 and arrives through the spherical lens 251, and repeatedly outputs a detection signal indicating a one-dimensional interference image at a predetermined line rate.

The imaging unit 254 is, for example, a line sensor in which a plurality of pixels are disposed one-dimensionally. Further, the imaging unit 254 may be a two-dimensional sensor which is configured to read any one line of pixels arranged in a direction intersecting with the moving direction of the image of the cell 30 on the light receiving plane. Hereinbelow, the description will be given assuming that the imaging unit 254 is a line sensor, however, in a case where the imaging unit 254 is a two-dimensional sensor, the above-described one-line pixels will be considered as a line sensor.

The analysis unit 261 inputs the detection signal output repeatedly from the imaging unit 254, and generates the two-dimensional image on the basis of the one-dimensional interference image at each time point indicated by the detection signal. The analysis unit 261 generates, for example, the two-dimensional phase image of the cell 30 as the two-dimensional image by the phase retrieval method (see Non Patent Documents 1 to 3) on the basis of the one-dimensional interference image at each time point. Examples of the phase retrieval method include a phase shift method, a Fourier transform method, and a Hilbert transform method. Further, for example, the analysis unit 261 generates the two-dimensional interference image on the basis of the plurality of one-dimensional interference images at a plurality of time points.

In order for the analysis unit 261 to generate the phase image with a high accuracy on the basis of the interference image, the frequency Ω of the phase difference change by the Doppler shift is preferably ⅓ times the line rate of the imaging unit 254 or less. Further, the frequency Ω is preferably ¼ times the line rate. The phase image is generated as already described in the first configuration example.

The analysis unit 261 analyzes a shape (an external form, a shape of a nucleus, or the like) of the cell 30 on the basis of the two-dimensional phase image to determine whether the cell 30 is the CTC. Further, the analysis unit 261 preferably performs a correction process in order to reduce a temporal or spatial influence of noises in the phase image. The correction process is the same as already described in the first configuration example.

The analysis unit 261 may be configured by a general-purpose computer, or may be configured by a dedicated device using, for example, a microcomputer or an FPGA. In a case where a dedicated device is used, the analysis unit 261 can generate and analyze the phase image at a high speed, and for example, the analysis unit can both input the detection signal from the imaging unit 254 and generate the phase image on the basis of the input detection signal in parallel in real time.

Further, the analysis unit 261 controls the linear motion stage 242 to move the mirror 241 in one direction during an exposure period of the imaging unit 254, and to move the mirror 241 in the reverse direction during a period of an A/D conversion and data transfer of the imaging unit 254.

The display unit 262 is, for example, a display which displays the interference image and the phase image generated by the analysis unit 261, and displays an analysis result on the basis of the phase image by the analysis unit 261. When the analysis unit 261 determines that the cell 30 is the CTC, the display unit 262 may make a sound or emit light to display the fact.

Even in the third configuration example, similarly to the case of the first configuration example, it is possible to easily generate an excellent phase image of the cell 30 which flows in the flow path 10 with the fluid 20.

(Fourth Configuration Example of First Observation Apparatus 40)

Figure 18:
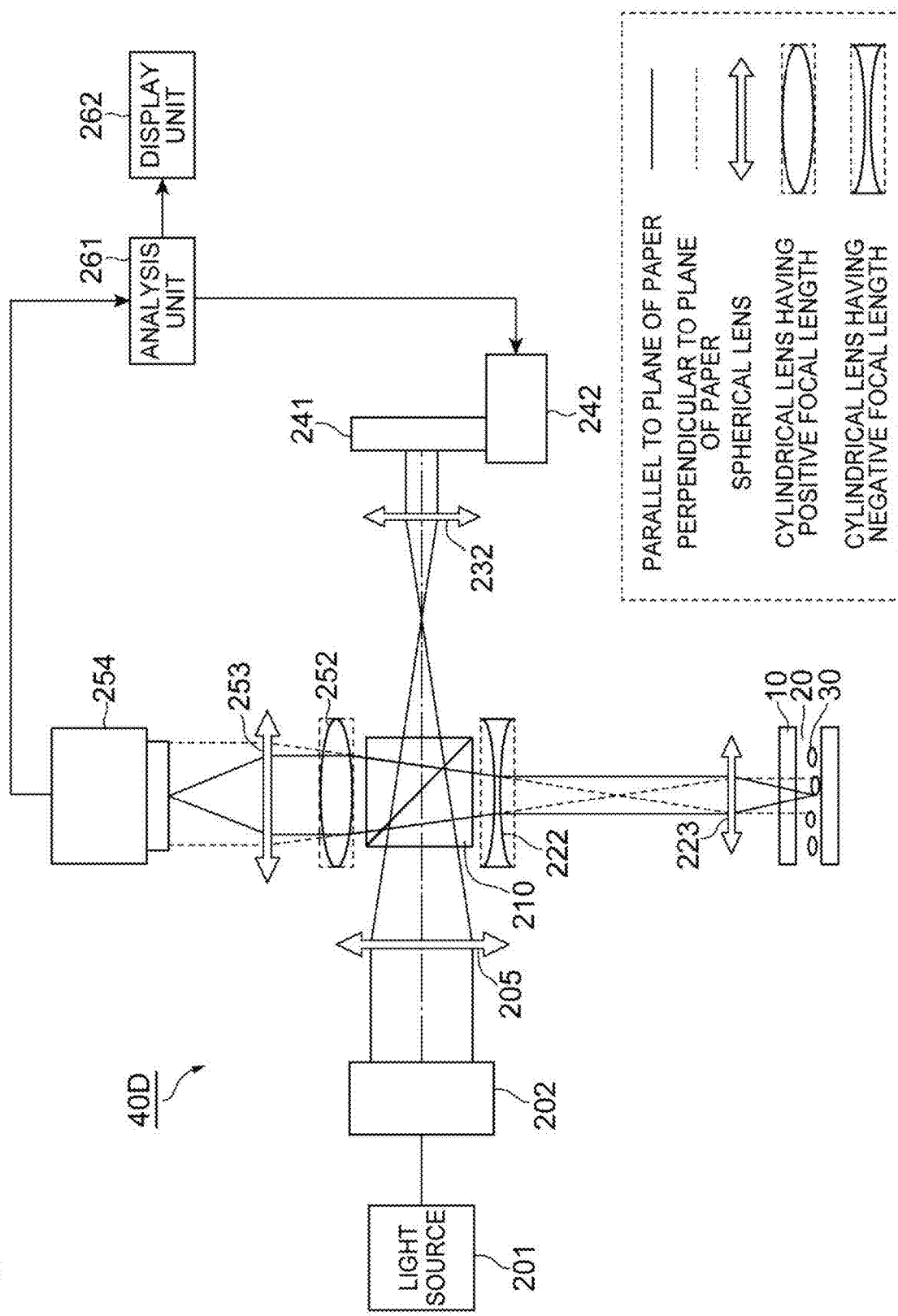
FIG. 18 is a diagram illustrating a fourth configuration example of the first observation apparatus 40.

FIG. 18 is a diagram illustrating a fourth configuration example of the first observation apparatus 40. The fourth configuration example is a modification of the third configuration example. An observation apparatus 40D of the fourth configuration example includes a spherical lens 205 on the optical path between the collimator 202 and the splitting-combining unit 210, a cylindrical lens 222 and a spherical lens 223 on the optical path of the first split light between the splitting-combining unit 210 and the flow path 10, a spherical lens 232 on the optical path of the second split light between the splitting-combining unit 210 and the mirror 241, and a cylindrical lens 252 and a spherical lens 253 on the optical path of the combined light between the splitting-combining unit 210 and the imaging unit 254. Even in this drawing, the change of the light beam width in the direction parallel to the plane of paper is depicted with a solid line, and the change of the light beam width in the direction perpendicular to the plane of paper is depicted with a dashed line.

The spherical lens 205 inputs the light output from the collimator 202, and converges and outputs the light to the splitting-combining unit 210.

The cylindrical lens 222 is a concave lens having a negative focal length. The cylindrical lens 222 inputs the first split light output from the splitting-combining unit 210, outputs the first split light as parallel light in the direction parallel to the plane of paper, and converges the first split light in the direction perpendicular to the plane of paper. The spherical lens 223 inputs the first split light output from the cylindrical lens 222, converges the first split light in the direction parallel to the plane of paper, outputs the first split light as parallel light in the direction perpendicular to the plane of paper, and outputs the first split light to the flow path 10. The spherical lens 223 and the cylindrical lens 222 input the first split light which is reflected on the bottom surface of the flow path 10, and output the first split light to the splitting-combining unit 210.

The spherical lens 232 inputs the second split light output from the splitting-combining unit 210, and outputs the second split light as parallel light to the mirror 241. The spherical lens 232 inputs the second split light which is reflected on the mirror 241, and outputs the second split light to the splitting-combining unit 210.

The splitting-combining unit 210 inputs the first split light which arrives from the cylindrical lens 222, inputs the second split light which arrives from the spherical lens 232, combines the first split light and the second split light, and outputs the combined light to the cylindrical lens 252.

The cylindrical lens 252 is a convex lens having a positive focal length. The cylindrical lens 252 inputs the combined light output from the splitting-combining unit 210, outputs the combined light as parallel light in the direction parallel to the plane of paper, and diverges the combined light in the direction perpendicular to the plane of paper. The spherical lens 253 inputs the combined light output from the cylindrical lens 252, converges the combined light in the direction parallel to the plane of paper, and the combined light is entered on a light receiving plane of the imaging unit 254 using the combined light as parallel light in the direction perpendicular to the plane of paper. The cell 30 in the flow path 10 and the light receiving plane of the imaging unit 254 are in an imaging relation by the spherical lens 223, the cylindrical lens 222, the cylindrical lens 252, and the spherical lens 253 which are on the optical path therebetween.

Even in the fourth configuration example, similarly to the case of the first configuration example, it is possible to easily generate an excellent phase image of the cell 30 which flows in the flow path 10 with the fluid 20.

The cell observation system and the cell observation method are not limited to the above embodiments and the configuration examples, and various modifications can be made.

The cell observation system of the above embodiment is a system for observing a cell moving in a flow path with a fluid, and is configured to include (1) a first observation apparatus including a line camera and a first optical system, and configured to capture an image of the cell using the line camera to acquire and output first imaging data, (2) a second observation apparatus including an area camera and a second optical system, and configured to capture an image of the cell using the area camera to acquire second imaging data, and (3) a control device configured to analyze the first imaging data output from the first observation apparatus to determine whether the cell satisfies a specific condition, instruct the area camera to output the second imaging data of the cell determined to satisfy the specific condition, and analyze the second imaging data output from the second observation apparatus to determine whether the cell is a specific cell.

In the above cell observation system, the area camera may be configured to capture the image at a position on a downstream side from an imaging position of the line camera in a moving direction of the cell in the flow path, receive the output instruction from the control device, and capture the image of the cell over a predetermined period of time to output the second imaging data.

In the above cell observation system, the area camera may be configured to sequentially store the second imaging data at each time point in a built-in memory of a ring buffer type, receive the output instruction from the control device, and output the second imaging data over a predetermined period of time stored in the memory.

In this case, the area camera may be configured to capture the image at a position on an upstream or downstream side from an imaging position of the line camera in a moving direction of the cell in the flow path. Further, the area camera may be configured to capture the image at the same position as an imaging position of the line camera in a moving direction of the cell in the flow path. Further, in the latter case, at least parts of the first optical system and the second optical system may be configured in common.

In the above cell observation system, the flow path may include a branch flow path through which a cell determined as the specific cell by the control device selectively flows.

In the above cell observation system, the control device may be configured to analyze the first imaging data to determine whether there is a cell suspected as a cancer cell, and analyze the second imaging data to determine whether the cell is a cancer cell.

The cell observation method of the above embodiment is a method for observing a cell moving in a flow path with a fluid, and is configured to include (1) a first determination step of determining whether the cell satisfies a specific condition by analyzing first imaging data output from a first observation apparatus, the first observation apparatus including a line camera and a first optical system, and configured to capture an image of the cell using the line camera to acquire and output the first imaging data, (2) an instruction step of instructing a second observation apparatus to output second imaging data for the cell determined to satisfy the specific condition, the second observation apparatus including an area camera and a second optical system, and configured to capture an image of the cell using the area camera to acquire the second imaging data, and (3) a second determination step of analyzing the second imaging data output from the second observation apparatus to determine whether the cell is a specific cell.

In the above cell observation method, the area camera may be configured to capture the image at a position on a downstream side from an imaging position of the line camera in a moving direction of the cell in the flow path, receive the output instruction in the instruction step, and capture the image of the cell over a predetermined period of time to output the second imaging data.

In the above cell observation method, the area camera may be configured to sequentially store the second imaging data at each time point in a built-in memory of a ring buffer type, receive the output instruction in the instruction step, and output the second imaging data over a predetermined period of time stored in the memory.

In this case, the area camera may be configured to capture the image at a position on an upstream or downstream side from an imaging position of the line camera in a moving direction of the cell in the flow path. Further, the area camera may be configured to capture the image at the same position as an imaging position of the line camera in a moving direction of the cell in the flow path. Further, in the latter case, at least parts of the first optical system and the second optical system may be configured in common.

In the above cell observation method, the flow path may include a branch flow path through which a cell determined as the specific cell in the second determination step selectively flows.

In the above cell observation method, in the first determination step, the first imaging data may be analyzed to determine whether there is a cell suspected as a cancer cell, and in the second determination step, the second imaging data may be analyzed to determine whether the cell is a cancer cell.

The embodiments may be used as a cell observation system and a cell observation method which can observe a large number of cells, and can be suitably used to identify a specific cell (cancer cell).

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A cell observation method for observing a cell moving in a flow path with a fluid, comprising:
    obtaining first imaging data for a cell moving in the flow path during a first imaging period, the first imaging data including a plurality of first images obtained using a line camera and a first objective lens at a first imaging position with respect to a moving direction of the cell in the flow path;
    obtaining second imaging data for the cell during a second imaging period that overlaps with the first imaging period and is longer than the first imaging period, the second imaging data including a plurality of second images obtained using an area camera and a second objective lens at a second imaging position with respect to the moving direction of the cell in the flow path;
    sequentially storing the second imaging data obtained during the second imaging period in a built-in memory of a ring buffer type of the area camera;
    determining whether the cell is suspected as a cancer cell by analyzing the first imaging data sequentially output from the line camera; and
    in response to determining that the cell is suspected as a cancer cell,
        suspending the storing of the second imaging data in the built-in memory of the area camera;
        outputting, from the area camera, a portion of the stored second imaging data;
        in response to outputting the portion of the stored second imaging data from the area camera, restarting the obtaining of second imaging data and the storing of the second imaging data in the built-in memory of the area camera; and
        determining whether the cell is a cancer cell by analyzing the portion of the stored second imaging data output from the area camera,
    wherein the second imaging position is the same as the first imaging position with respect to the moving direction of the cell in the flow path.

2. The cell observation method according to claim 1, wherein the first objective lens and the second objective lens are configured as a common lens.

3. The cell observation method according to claim 1, wherein the flow path includes a branch flow path through which the cell determined as the specific cell selectively flows.

* * * * *